United States Patent
Shin et al.

(10) Patent No.: US 6,571,608 B2
(45) Date of Patent: Jun. 3, 2003

(54) SINGLE RISER/SINGLE CAPILLARY VISCOMETER USING MASS DETECTION OR COLUMN HEIGHT DETECTION

(75) Inventors: Sehyun Shin, Bryn Mawr, PA (US); Young Cho, Cherry Hill, NJ (US); Kenneth Kensey, Malvern, PA (US); William N. Hogenauer, Gilbertsville, PA (US); Sangho Kim, Philadelphia, PA (US)

(73) Assignee: Rheologics, Inc., Exton, PA (US)

( * ) Notice: Subject to any disclaimer, the term of this patent is extended or adjusted under 35 U.S.C. 154(b) by 0 days.

(21) Appl. No.: 10/156,165

(22) Filed: May 28, 2002

(65) Prior Publication Data

US 2002/0184941 A1 Dec. 12, 2002

Related U.S. Application Data

(60) Division of application No. 09/897,164, filed on Jul. 2, 2001, now Pat. No. 6,484,565, which is a continuation-in-part of application No. 09/789,350, filed on Feb. 21, 2001, now abandoned, application No. 10/156,165, which is a continuation-in-part of application No. 09/439,795, filed on Nov. 12, 1999, now Pat. No. 6,322,524.

(60) Provisional application No. 60/228,612, filed on Aug. 29, 2000.

(51) Int. Cl.[7] .......................... G01N 11/00; G01N 11/06
(52) U.S. Cl. ...................................... 73/54.01; 73/54.07
(58) Field of Search ............................ 73/54.01–54.43, 73/64.41–64.43

(56) References Cited

U.S. PATENT DOCUMENTS 1,810,992 A 6/1931 Dallwitz-Wegner (List continued on next page.)

FOREIGN PATENT DOCUMENTS

| CH | 229 225 A | 10/1943 |
|---|---|---|
| DE | 31 38 514 A1 | 4/1983 |
| DE | 33 31 659 A | 4/1985 |
| DE | 43 20 813 A1 | 1/1994 |
| DE | 198 09 530 C | 7/1999 |
| EP | 0 492 664 A | 7/1992 |
| EP | 0 654 286 A1 | 12/1994 |
| FR | 2 510 257 | 1/1983 |
| WO | WO 92/15878 | 9/1992 |
| WO | WO 94/20832 | 9/1994 |
| WO | WO 99/10724 | 3/1999 |

OTHER PUBLICATIONS

EP Search Report from corresponding International Application No. PCT/US01/25007, mailed Nov. 26, 2002.
Kensey, et al., Effects of Whole Blood Viscosity on Atherogenesis—J. of Invasive Cardiology, V. 9, 17, 1997.
Leonhardt, et al., Studies of Plasma Viscosity in Primary Hyperlipoproteinaemia—Atherosclerosis, V. 28, 29–40, 1977.

(List continued on next page.)

*Primary Examiner*—Helen Kwok
*Assistant Examiner*—Jay L Politzer
(74) *Attorney, Agent, or Firm*—Caesar Rivise, Bernstein, Cohen & Pokotilow, Ltd.

(57) ABSTRACT

An apparatus and method for determining the viscosity of a fluid over plural shear rates caused by a decreasing pressure differential by monitoring the movement of the fluid through a riser tube and a capillary tube. The movement can be monitored by detecting the changing weight of the fluid, using a precision balance or load cell, as it moves through the riser tube and capillary tube into a fluid collector; or, alternatively, the movement can be monitored by detecting the changing level of a fluid column in the riser tube using a column level detector. A processor then uses the changing weight or height data, along with the dimensions of the capillary tube and a dimension of the riser tube, to determine the viscosity of the fluid. In addition, apparatus and methods for determining fluid viscosity online and fluid mixture homogeneity online are also described.

17 Claims, 18 Drawing Sheets

U.S. PATENT DOCUMENTS

| | | |
|---|---|---|
| 2,343,061 A | 2/1944 | Irany |
| 2,696,734 A | 12/1954 | Brunstrum et al. |
| 2,700,891 A | 2/1955 | Shafer |
| 2,934,944 A | 5/1960 | Eolkin |
| 3,071,961 A | 1/1963 | Heigl et al. |
| 3,116,630 A | 1/1964 | Piros |
| 3,137,161 A | 6/1964 | Lewis et al. |
| 3,138,950 A | 6/1964 | Welty et al. |
| 3,277,694 A | 10/1966 | Cannon et al. |
| 3,286,511 A | 11/1966 | Harkness |
| 3,342,063 A | 9/1967 | Smythe et al. |
| 3,435,665 A | 4/1969 | Tzentis |
| 3,520,179 A | 7/1970 | Reed |
| 3,604,247 A | 9/1971 | Gramain et al. |
| 3,666,999 A | 5/1972 | Moreland, Jr. et al. |
| 3,680,362 A | 8/1972 | Geerdes et al. |
| 3,699,804 A | 10/1972 | Gassmann et al. |
| 3,713,328 A | 1/1973 | Aritomi |
| 3,720,097 A | 3/1973 | Kron |
| 3,782,173 A | 1/1974 | Van Vessem et al. |
| 3,839,901 A | 10/1974 | Finkle et al. |
| 3,864,962 A | 2/1975 | Stark et al. |
| 3,908,441 A | 9/1975 | Virloget |
| 3,911,728 A | 10/1975 | Fixot |
| 3,952,577 A | 4/1976 | Hayes et al. |
| 3,967,934 A | 7/1976 | Seitz et al. |
| 3,990,295 A | 11/1976 | Renovanz et al. |
| 3,999,538 A | 12/1976 | Philpot, Jr. |
| 4,083,363 A | 4/1978 | Philpot, Jr. |
| 4,149,405 A | 4/1979 | Ringrose |
| 4,165,632 A | 8/1979 | Weber et al. |
| 4,193,293 A | 3/1980 | Cavallari |
| 4,207,870 A | 6/1980 | Eldridge |
| 4,302,965 A | 12/1981 | Johnson et al. |
| 4,341,111 A | 7/1982 | Husar |
| 4,417,584 A | 11/1983 | Cathignol et al. |
| 4,426,878 A | 1/1984 | Price et al. |
| 4,432,761 A | 2/1984 | Dawe |
| 4,461,830 A | 7/1984 | Philpot, Jr. |
| 4,495,798 A | 1/1985 | Ehrgott |
| 4,517,830 A | 5/1985 | Gunn et al. |
| 4,519,239 A | 5/1985 | Kiesewetter et al. |
| 4,554,821 A | 11/1985 | Kiesewetter et al. |
| H93 H | 7/1986 | Matta et al. |
| 4,616,503 A | 10/1986 | Plungis et al. |
| 4,637,250 A | 1/1987 | Irvine, Jr. et al. |
| 4,643,021 A | 2/1987 | Mattout |
| 4,662,030 A | 5/1987 | Cooper et al. |
| 4,680,957 A | 7/1987 | Dodd |
| 4,680,958 A | 7/1987 | Ruelle et al. |
| 4,750,351 A | 6/1988 | Ball |
| 4,856,322 A | 8/1989 | Langrick et al. |
| 4,858,127 A | 8/1989 | Kron et al. |
| 4,884,577 A | 12/1989 | Merrill |
| 4,899,575 A | 2/1990 | Chu et al. |
| 4,947,678 A | 8/1990 | Hori et al. |
| 5,099,698 A | 3/1992 | Kath et al. |
| 5,181,415 A | 1/1993 | Esvan et al. |
| 5,222,497 A | 6/1993 | Ono |
| 5,224,375 A | 7/1993 | You et al. |
| 5,257,529 A | 11/1993 | Taniguchi et al. |
| 5,271,398 A | 12/1993 | Schlain et al. |
| 5,272,912 A | 12/1993 | Katsuzaki |
| 5,327,778 A | 7/1994 | Park |
| 5,333,497 A | 8/1994 | Br nd Dag A et al. |
| 5,365,776 A | 11/1994 | Lehmann et al. |
| 5,421,328 A | 6/1995 | Bedingham |
| 5,443,078 A | 8/1995 | Uflacker |
| 5,447,440 A | 9/1995 | Davis et al. |
| 5,491,408 A | 2/1996 | Rousseau |
| 5,494,639 A | 2/1996 | Grzegorzewski |
| 5,629,209 A | 5/1997 | Braun, Sr. et al. |
| 5,686,659 A | 11/1997 | Neel et al. |
| 5,792,660 A | 8/1998 | Spillert et al. |
| 6,019,735 A | 2/2000 | Kensey et al. |
| 6,077,234 A | 6/2000 | Kensey |
| 6,152,888 A | 11/2000 | Kensey et al. |
| 6,193,667 B1 | 2/2001 | Kensey |
| 6,200,277 B1 | 3/2001 | Kensey |
| 6,261,244 B1 | 7/2001 | Kensey et al. |
| 6,322,524 B1 | 11/2001 | Kensey et al. |
| 6,322,525 B1 | 11/2001 | Kensey et al. |
| 6,402,703 B1 | 6/2002 | Kensey et al. |
| 6,412,336 B2 | 7/2002 | Shin et al. |
| 6,428,488 B1 | 8/2002 | Kensey et al. |
| 6,450,974 B1 | 9/2002 | Kim et al. |
| 6,484,566 B1 | 11/2002 | Shin et al. |

OTHER PUBLICATIONS

Ernst, et al., Cardiovascular Risk Factors and Hemorheology: Physical fitness, Stress & Obesity—Atherosclerosis V. 59, 263–269, 1986.

Levenson, et al., Cigarette Smoking & Hypertension—Atherosclerosis V. 7, 572–577, 1987.

Rillaerts, et al., Blood Viscosity in Human Obesity; relation to glucose Tolerance & Insulin Status—Int'l Jrnl of Obesity, V. 13, 739–741, 1989.

Rosenson, R., Viscosity & Ischemic Heart Disease—Jrnl of Vascular Medicine & Biology, V. 4, 206–212, 1993.

Letcher, et al., Direct Relationship between Blood Pressure & Blood Viscosity in Normal and Hypertensive Subjects—Amer. Jrnl of Medicine, V.70, 1195–1203, Jun. 1981.

Zwick, K.J., The Fluid Mechanics of Bonding With Yield Stress Exposies, Dissortation—Univ of Penna, PA, USA, 1–142, 1996.

Yarnell, et al., Fibrinogen, Viscosity & White Blood Cell Count Are Major Risk Factors for Ischemic Heart Disease—Circulation, V. 83, No. 3, Mar. 1991.

Tangney, et al., Postprandial changes in Plasma and Serum Viscosity and Plasma Lipids and Lipoproteins After an Acute Test Meal—Amer. Jrnl. Of Clinical Nutrition, V.65, pp 36–40, 1997.

Seplowitz, et al., Effects of Lipoproteins on Plasma Viscosity—Atherosclerosis, V. 38, pp 89–95, 1981.

Rosenson, et al, Hyperviscosity Syndrome in Hypercholesterolemic Patient with Primary Biliary Cirrhosis—Gastroenterology, V. 98, No. 5, 1990.

Lowe, et al., Blood Viscosity & Risk of Cardiovascular Events: Edinburgh Artery Study British Jrnl of Haematology, V. 96, 168–173, 1997.

Koenig, W., Blood Rheology Assoc. With Cardiovascular Risk Factors & Chronic Cardiovascular Disease; Results of Epidemiologic Cross-sectional Study—Am. Coll. Angiology, Paradise Is., Bahamas—Oct. 1987.

Hell, K., Importance of Blood Visco–elasticity in Arteriosclerosis Internl Coll of Angiology, Montreaux, Switzerland, Jul. 1987.

Delaunois, A., Thermal method for Continuous Blood Velocity Measurements in Large Blood Vessels, and Cardiac Output Determination—Med. & Biol. Engineering, Mar. 1973, vol. 11, 201–205.

Nerem, et al., Fluid Mechanics in Atherosclerosis—Handbook of Bioengineering, Chap. 21, 20.24 to 21.22.

Litt, et al., Theory & Design of Disposable Clinical Blood Viscometer–Biorheology, vol. 25, 697–712, 1988.

Cooke, et al., Automated Measurement of Plasma Viscosity by Capillary Viscometer—J. Clinical Pathology, vol. 31, 1213–1216, 1988.

Jiminez, et al., A Novel Computerized Viscometer/Rheometer –Rev. Sci. Instru. vol. 65 (1), pp. 229–241, Jan. 1994.

Harkness, A New Instrument for the Measurement of Plasma–Viscosity—The Lancet, New Inventions, pp. 280–281, Aug. 10, 1963.

Pringle, et al., Blood Viscosity & Raynaud's Disease—The Lancet, May 1965.

Walker, et al., Measurement of Blood.

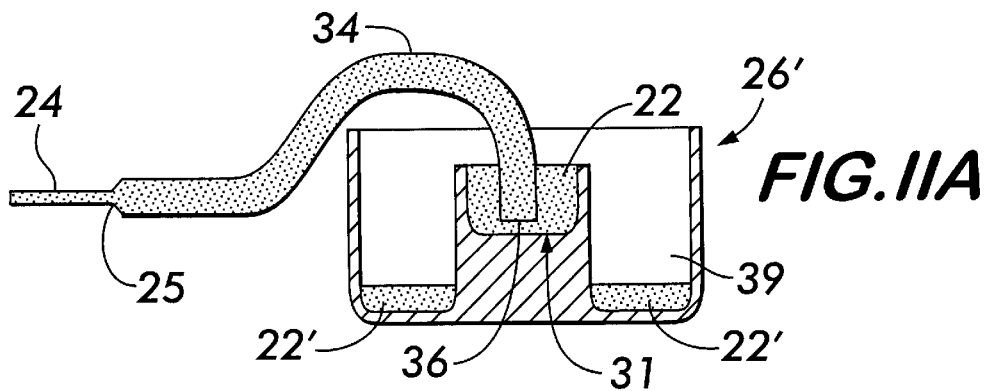
*FIG.IIA*
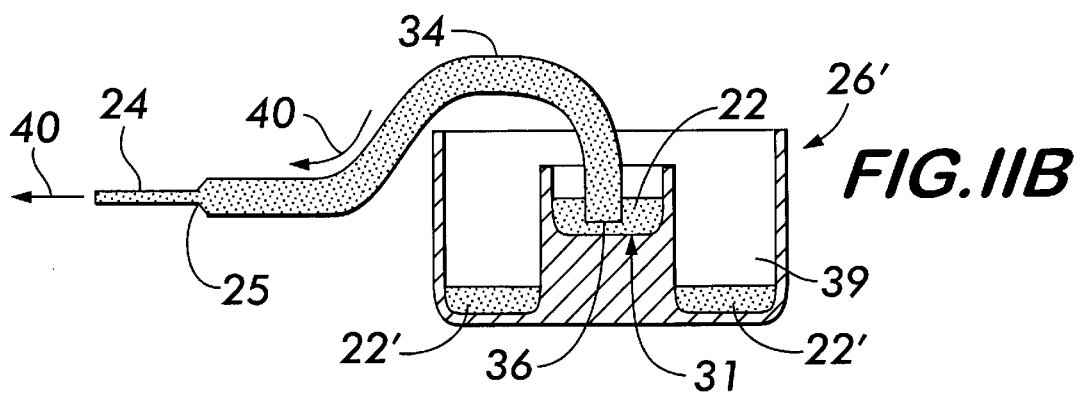
*FIG.IIB*
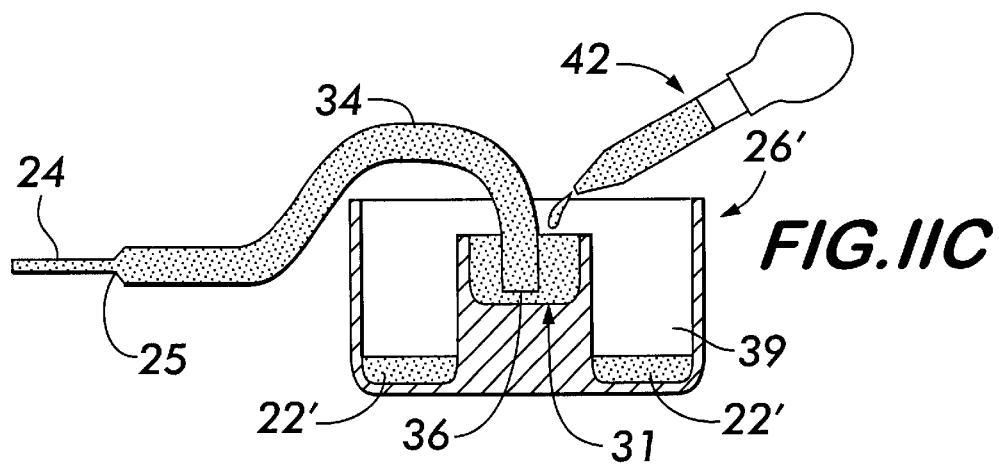
*FIG.IIC*
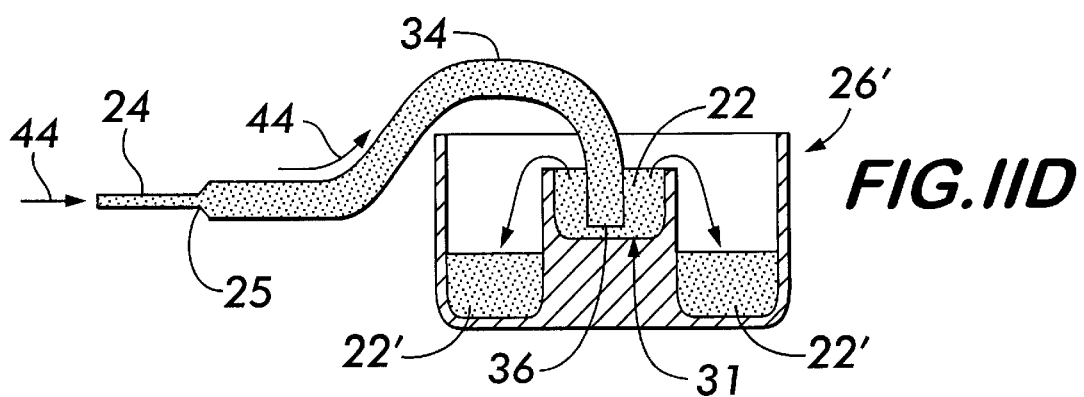
*FIG.IID*

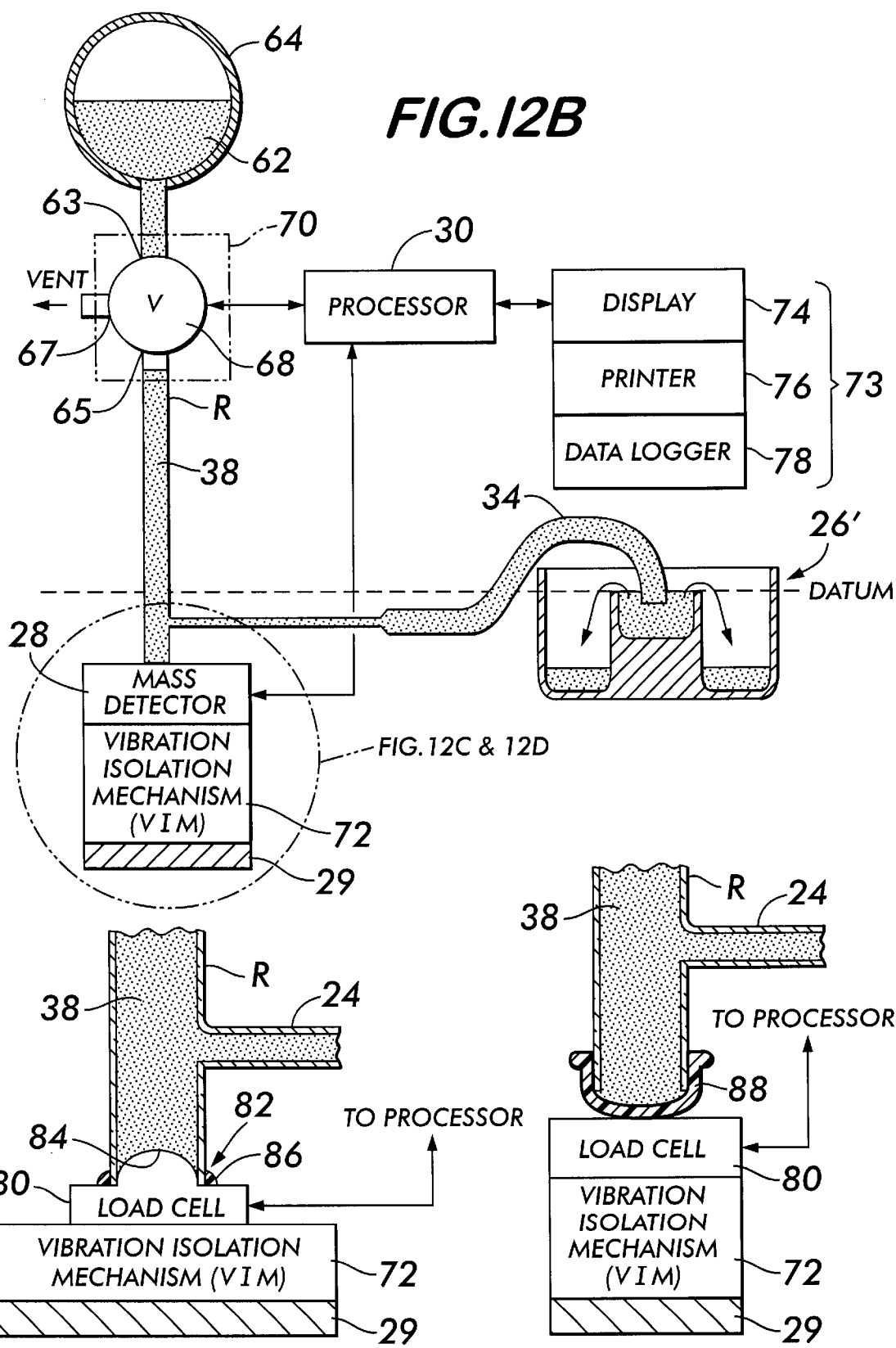

SINGLE RISER/SINGLE CAPILLARY VISCOMETER USING MASS DETECTION OR COLUMN HEIGHT DETECTION

RELATED APPLICATIONS

This application is a divisional application of Ser. No. 09/897,164, filed on Jul. 2, 2001 now U.S. Pat. No. 6,484,565 entitled SINGLE RISER/SINGLE CAPILLARY VISCOMETER USING MASS DETECTION OR COLUMN HEIGHT DETECTION, which is a Continuation-in-Part of application Ser. No. 09/789,350, filed on Feb. 21, 2001, now abandoned, entitled MASS DETECTION CAPILLARY VISCOMETER which in turn is a utility application based on Provisional Application Serial No. 60/228,612 filed Aug. 29, 2000 entitled MASS DETECTION CAPILLARY VISCOMETER. This application is also a Continuation-in-Part of application Ser. No. 09/439,795, filed Nov. 12, 1999 now U.S. Pat. No. 6,322,524, entitled, DUAL RISER/SINGLE CAPILLARY VISCOMETER. The entire disclosures of all the above applications are incorporated by reference herein.

SPECIFICATION

BACKGROUND OF THE INVENTION

A capillary viscometer is commonly used because of its inherent features such as simplicity, accuracy, similarity to process flows like extrusion dies, no free surface, etc. Viscous flow in capillary viscometry is firmly established both theoretically and experimentally. C. W. Macosko, *Rheology: Principles, Measurements, and Applications* (VCH, 1993). In fact, the capillary viscometer was the first viscometer and this device remains the most common for measuring viscosity for polymer solutions and other non-Newtonian fluids. However, most existing capillary viscometers produce viscosity measurement a shear rate at a time. In the case of Newtonian fluids the observation of the rate of flow at a single pressure drop is sufficient to define the flow behavior. However, in the case of non-Newtonian fluids, viscosity measurements need to be performed over a range of shear rates. In order to measure viscosity over a range of shear rates, it is necessary to repeat the measurement by varying either the driving pressure head or the capillary tube diameter, which leads to a time-consuming measurement requiring intensive labor. Hence, these methods are not suited for measuring the rheology of polymer fluids that may exhibit shear-dependent viscosities. Furthermore, application of such techniques often requires relatively large volumes of the test fluids. Therefore, there has been a need to develop a simple and labor-free viscometer which can measure the viscosity of fluids over shear rates at a time.

In U.S. Pat. No. 6,019,735 (Kensey et al.) and U.S. Pat. No. 6,077,234 (Kensey et al.), which are assigned to the same Assignee, namely Visco Technologies, Inc., of the present invention, there is disclosed a scanning-capillary-tube viscometer for measuring the viscosity of a fluid, e.g., circulating blood of a living being. Among other things, this scanning capillary tube viscometer discloses an apparatus that monitors the changing height of a column of fluid versus time in a riser that is in fluid communication with a living being's circulating blood. A further improvement of this type of scanning capillary tube viscometer is disclosed in application Ser. No. 09/439,735 entitled DUAL RISER/SINGLE CAPILLARY VISCOMETER, which is assigned to the same Assignee as the present invention, namely, Visco Technologies, Inc. and whose entire disclosure is incorporated by reference herein. In that application, a U-shaped tube structure is utilized that generates a falling and rising column of test fluid that is driven by a decreasing pressure differential for moving these columns of fluid through a plurality of shear rates, which is necessary for non-Newtonian fluid (e.g., blood) viscosity determinations. Such an apparatus can produce viscosity data in a low shear range (e.g., approximately 0.02 s$^{-1}$).

However, there is a need for an alternative mechanism of monitoring the changing column of fluid over time, such as detecting the changing mass of the column of fluid or the changing height of the column of fluid, as set forth in the present application. The key principle of the single riser/single capillary viscometer is that both flow rate and pressure drop at a capillary tube can be determined by the monitoring of collected fluid mass variation with time using a load cell, or by the monitoring of the changing height with time of the fluid column height. Thus, there also remains a need to develop a viscosity determination in a quasi-steady capillary flow and to measure the viscosity of non-Newtonian fluids (e.g., polymer solutions, circulating blood of a living being, etc.) over a range of shear rates.

SUMMARY OF THE INVENTION

An apparatus for detecting the movement of a fluid at plural shear rates caused by a decreasing pressure differential. The apparatus comprises: a lumen (e.g., a riser tube) having a first end and a second end and being positioned at an angle to a horizontal reference greater than zero degrees; a flow restrictor (e.g., a capillary tube) having an inlet and an outlet wherein the inlet is in fluid communication with the second end and wherein the outlet is arranged to deliver any fluid that passes therethrough to a collector; the lumen and the flow restrictor being initially occupied by a continuous, non-moving sample of fluid therein; a sensor (e.g., a precision balance, load cell, or level detector) for detecting the movement of the fluid over time once the sample of fluid begins moving and passes from the outlet into the collector; and the first end being exposed to atmospheric pressure creating a pressure differential between the first end and the outlet, whereby the sample of fluid moves through the lumen and the flow restrictor at a first shear rate caused by the pressure differential and wherein the movement of fluid causes the pressure differential to decrease from the first shear rate for generating the plural shear rates.

An apparatus for determining the viscosity of a fluid over plural shear rates using a decreasing pressure differential. The apparatus comprises: a lumen (e.g., a riser tube) having a first end and a second end and is positioned at an angle to a horizontal reference greater than zero degrees and wherein the lumen has a first known dimension; a flow restrictor (e.g., a capillary tube) having an inlet and an outlet and wherein the inlet is in fluid communication with the second end and wherein the outlet is arranged to deliver any fluid that passes therethrough to a collector, and wherein the flow restrictor includes some known dimensions; wherein the lumen and the flow restrictor are initially occupied by a continuous, non-moving sample of fluid therein; a sensor (e.g., a precision balance, load cell or a level detector) for detecting the movement of the fluid over time once the sample of fluid begins moving and passes from the outlet into the collector, and wherein the sensor generates data relating to the movement of the fluid over time; the first end is then exposed to atmospheric pressure which creates a pressure differential between the first end and the outlet, and wherein the sample of fluid moves through the lumen and the flow restrictor at a first shear rate caused by the pressure differential, and wherein the movement of fluid causes the pressure differential to decrease from the first shear rate for generating the plural shear rates; and a computer, coupled to the sensor, for calculating the viscosity of the fluid based on the data relating to the movement of the fluid over time, the first known dimension of the lumen and the some known dimensions of the flow restrictor.

A method for detecting the movement a fluid at plural shear rates caused by a decreasing pressure differential. The method comprises the steps of: (a) providing a lumen (e.g., a riser tube) having a first end and a second end and positioned at an angle to a horizontal reference greater than zero degrees; (b) coupling an inlet of a flow restrictor of (e.g., a capillary tube), having an outlet, to the second end of the lumen; (c) positioning the outlet to deliver any fluid flowing through the outlet into the collector; (d) coupling a suction source to the first end and activating the source to draw up a sample of the fluid from the collector to form a continuous sample of fluid that occupies the lumen and the flow restrictor, thereby establishing a pressure differential between the first end and the outlet; (e) exposing the first end to atmospheric pressure to cause the sample of fluid to move through the lumen and the flow restrictor at a first shear rate caused by the pressure differential, wherein the movement of fluid causes the pressure differential to decrease from the first shear rate for generating the plural shear rates; and (f) providing a sensor (e.g., a precision balance, a load cell, or a level detector) for detecting the movement of fluid over time as the sample of fluid moves and passes through the outlet into the collector.

A method for determining the viscosity of a fluid over plural shear rates caused by a decreasing pressure differential. The method comprising the steps of: (a) providing a lumen (e.g., a riser tube) having a first end and a second end and positioned at an angle to a horizontal reference greater than zero degrees and wherein the lumen has a first known dimension; (b) coupling an inlet of a flow restrictor (e.g., a capillary tube), having an outlet, to the second end of the lumen and wherein the flow restrictor has some known dimensions; (c) submerging said outlet in a collector containing the fluid; (d) coupling a suction source to the first end and activating the source to draw up a sample of the fluid from the collector to form a continuous sample of fluid that occupies the lumen and the flow restrictor, thereby establishing a pressure differential between the first end and the outlet; (e) adding additional fluid to the collector to maintain the outlet submerged in the fluid in the collector; (f) exposing the first end to atmospheric pressure to cause the sample of fluid to move through the lumen and the flow restrictor at a first shear rate caused by the pressure differential, and wherein the movement of fluid causes the pressure differential to decrease from the first shear rate for generating the plural shear rates; (g) providing a sensor (e.g., a precision balance, a load cell or a level detector) for detecting the movement of the fluid over time as the sample of fluid passes through the outlet into the collector while maintaining the outlet submerged in the fluid in the collector; and (h) calculating the viscosity of the fluid based on the generated data, the first known dimension and the some known dimensions.

A method for determining the online viscosity of a fluid flowing through a process. The method comprises the steps of: (a) providing a lumen (e.g., a tap-off plenum and/or riser) having a first end and a second end wherein the first end is coupled to the process through a valve and wherein the lumen is positioned at an angle to a horizontal reference greater than zero degrees and wherein the lumen has a first known dimension; (b) coupling an inlet of a flow restrictor (e.g., a capillary tube), having an outlet, to the second end of the lumen and wherein the flow restrictor has some known dimensions; (c) disposing a collector on a mass detector (e.g., a precision balance or load cell) and positioning the outlet to deliver any fluid flowing through the outlet into the collector; (d) opening the valve to allow a predetermined amount of fluid from the process to pass through the lumen and the flow restrictor and to collect in the collector to submerge the outlet and to form a continuous sample of fluid occupying the lumen and the flow restrictor and wherein the opening of the valve establishes a pressure differential between the first end and the outlet; (e) obtaining an initial weight of the collector by the mass detector; (f) further controlling the valve to vent the first end to atmospheric pressure to cause the sample of fluid to move through the lumen and the flow restrictor at a first shear rate caused by the pressure differential, and wherein the movement of fluid causes the pressure differential to decrease from the first shear rate for generating the plural shear rates; (g) detecting the changing weight of the collector over time as the sample of fluid passes through the outlet into the collector while maintaining the outlet submerged in the fluid in the collector; and (h) calculating the online viscosity of the fluid based on the changing weight of the collector over time, the first known dimension and the some known dimensions.

A method for determining the online viscosity of a fluid flowing through a process. The method comprises the steps of: (a) providing a lumen (e.g., a tap-off plenum and/or a riser) having a first end and a second end wherein the first end is coupled to the process through a valve and wherein the lumen is positioned at an angle to a horizontal reference greater than zero degrees, and wherein the lumen has a first known dimension; (b) coupling an inlet of a flow restrictor (e.g., a capillary tube), having an outlet, to the second end of the lumen, wherein the flow restrictor has some known dimensions; (c) disposing the lumen and the flow restrictor on a mass detector (e.g., a precision balance or load cell) and positioning the outlet to deliver any fluid flowing through the outlet into the collector; (d) opening the valve to allow a predetermined amount of fluid from the process to pass through the lumen and the flow restrictor and to collect in the collector to submerge the outlet and to form a continuous sample of fluid occupying the lumen and the flow restrictor, and wherein the opening of the valve establishes a pressure differential between the first end and the outlet; (e) obtaining an initial weight of the lumen and the flow restrictor by the mass detector; (f) further controlling the valve to vent the first end to atmospheric pressure to cause the sample of fluid to move through the lumen and the flow restrictor at a first shear rate caused by the pressure differential, and wherein the movement of fluid causes the pressure differential to decrease from the first shear rate for generating the plural shear rates; (g) detecting the changing weight of the lumen and the flow restrictor over time as the sample of fluid passes through the outlet into the collector while maintaining the outlet submerged in the fluid in the collector; and (h) calculating the online viscosity of the fluid based on the changing weight of the lumen and the flow restrictor over time, the first known dimension and the some known dimensions.

An apparatus for determining the online homogeneity of a fluid mixture flowing through a process. The apparatus comprises: a lumen (e.g., a tap-off plenum and/or riser) having a first end and a second end and is positioned at an angle to a horizontal reference greater than zero degrees, and wherein the lumen is coupled to the process at said first end; a flow restrictor (e.g., a capillary tube) having an inlet and an outlet, wherein the inlet is in fluid communication with the second end and wherein the outlet is arranged to deliver any fluid that passes therethrough to a collector; the lumen and the flow restrictor being initially occupied by a continuous, non-moving sample of fluid mixture therein that has been diverted from the process; a sensor (e.g., a precision balance or load cell) for detecting the changing weight of the lumen and the flow restrictor over time once the sample of fluid mixture begins moving and passes from the outlet into the collector, wherein the sensor generates data relating to the changing weight of the collector over time; the first end then being exposed to atmospheric pressure which creates a pressure differential between the first end and the outlet, wherein the sample of fluid mixture moves through the lumen and the flow restrictor at a first shear rate caused by the pressure differential, and wherein the movement of the fluid mixture causes the pressure differential to decrease from the first shear rate for generating plural shear rates; and a computer for statistically analyzing the data relating to the changing weight to determine if there is good or poor mixing of the fluid mixture.

A method for determining the online homogeneity of a fluid mixture flowing through a process. The method comprises the steps of: (a) providing a lumen (e.g., a tap-off plenum and/or riser) having a first end and a second end and positioned at an angle to a horizontal reference greater than zero degrees and wherein the first end is coupled to said process; (b) coupling an inlet of a flow restrictor (e.g., a capillary tube), having an outlet, to the second end of the lumen; (c) disposing the lumen and the flow restrictor on a mass detector (e.g., a precision balance or load cell) and positioning the outlet to deliver any fluid flowing through the outlet into a collector; (d) diverting a predetermined amount of the fluid mixture from the process into the lumen and the flow restrictor and to collect in the collector to form a continuous non-moving sample of fluid mixture occupying the lumen and the flow restrictor, and wherein the step of diverting establishes a pressure differential between the first end and the outlet; (e) obtaining an initial weight of the lumen and the flow restrictor by the mass detector; (f) exposing the first end to atmospheric pressure to cause the sample of fluid mixture to move through the lumen and the flow restrictor at a first shear rate caused by the pressure differential and wherein the movement of fluid causes the pressure differential to decrease from the first shear rate for generating plural shear rates; (g) detecting the changing weight of the lumen and the flow restrictor over time as the sample of fluid mixture passes through the outlet into the collector to form weight data over time; and (h) statistically analyzing the weight data to determine if there is good or poor mixing of the fluid mixture.

DESCRIPTION OF THE DRAWINGS

The invention of this present application will be readily appreciated as the same becomes better understood by reference to the following detailed description when considered in connection with the accompanying drawings wherein:

FIGS. 11A–11D depict the sequence of maintaining one end of an adaptor of the MDCV under the level of fluid collected in the fluid collector;

FIG. 12B depicts a functional diagram of a second online MDCV;

FIGS. 12C–12D depict alternative interfaces for detecting the mass of the column of the second online MCDV system, as well as the second MDCV embodiment of FIG. 9;

DETAILED DESCRIPTION OF THE PREFERRED EMBODIMENTS

Figure 1:
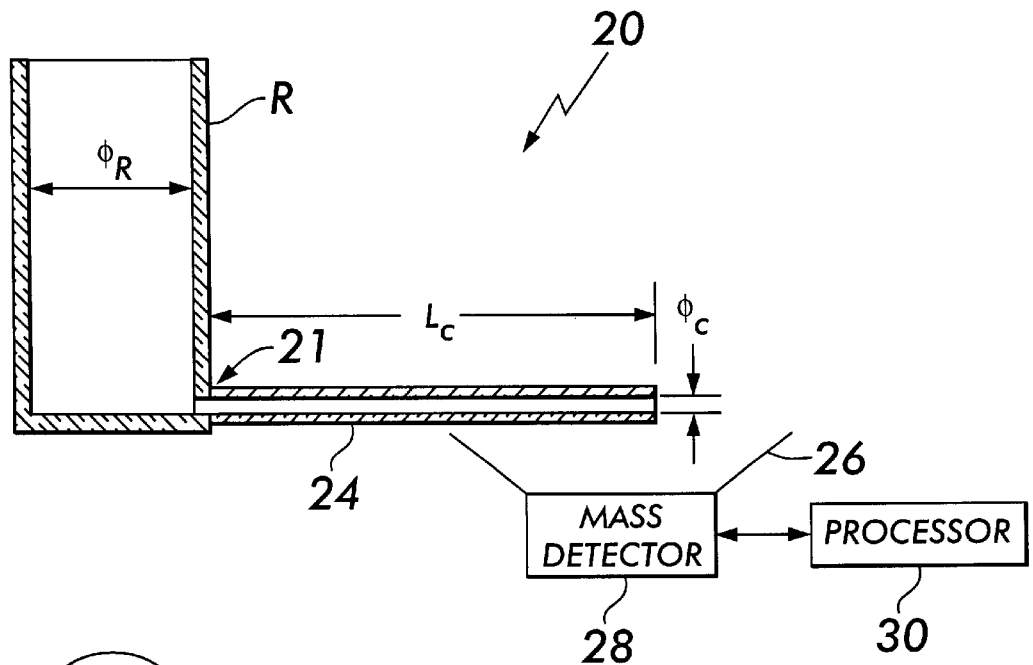
FIG. 1 is a cross-sectional view of a single riser/single capillary (SRSC) viscometer using mass detection which is also referred to as a mass detection capillary viscometer (MDCV)

The present invention, generally referred to as a single riser/single capillary (SRSC) viscometer, uses a single riser tube and a single flow restrictor (e.g., a capillary tube) structure for determining the viscosity of a test fluid.

Although the SRSC viscometer can be implemented in a number of ways, two exemplary apparatus/methods are set forth below. The first implementation uses the SRSC structure along with mass detection and hence is hereinafter referred to as a mass detection capillary viscometer (MDCV) 20. The second implementation uses the SRSC structure along with column height detection and hence is hereinafter referred to as a column height detection capillary (CHDC) viscometer 120.

Referring now in detail to the various figures of the drawing wherein like reference characters refer to like parts, there is shown at 20 a mass detecting capillary viscometer (MDCV).

Figure 2:
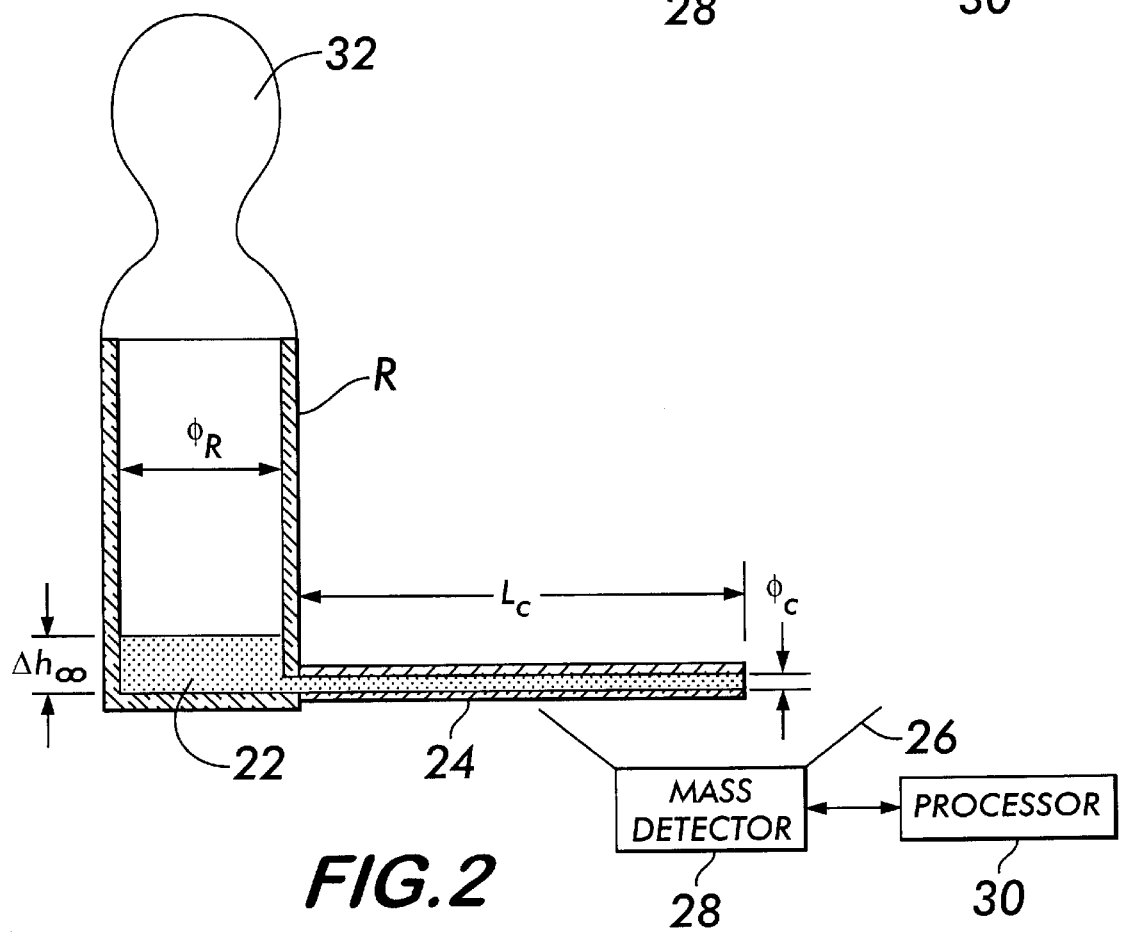
FIG. 2 is a cross-sectional view of the MDCV of FIG. 1 at the end of test run and wherein an auxiliary suction source is coupled to the invention to force out any remaining test fluid from the viscometer.

The MDCV 20 basically comprises a cylinder (e.g., a riser tube R) having a diameter, $\phi_R$, through which passes a test fluid (a portion of which 22 is shown in FIG. 2, and can be a Newtonian fluid or a non-Newtonian fluid) for viscosity analysis. The bottom of the riser tube R is coupled to an inlet 21 of a flow restrictor 24 (e.g., a capillary tube), having a diameter $\phi_c$ and a length $L_c$, that is positioned horizontally. The outlet 25 of the capillary tube 24 is open and is positioned over a collector 26. The collector 26 rests on a mass detector 28 (e.g., a precision balance, or load cell, such as The Adventurer™ by Ohaus Corporation of Florham Park, N.J.), that is communication with a processor 30. Thus, as the collector 26 collects more of the test fluid during the viscosity test run, the changing mass value is transmitted to the processor 30 from the mass detector 28 for viscosity determination; in particular, the mass detector 28 generates an electrical signal that corresponds to the mass variation with time.

It should be understood that the term "mass" may be interchanged with the term "weight" for purposes of this present invention. It should also be understood that the connection between the mass detector 28 and the processor 30 is bidirectional; this allows the processor 30 to reset the mass detector 28 in preparation for a new test run.

Figure 1A:
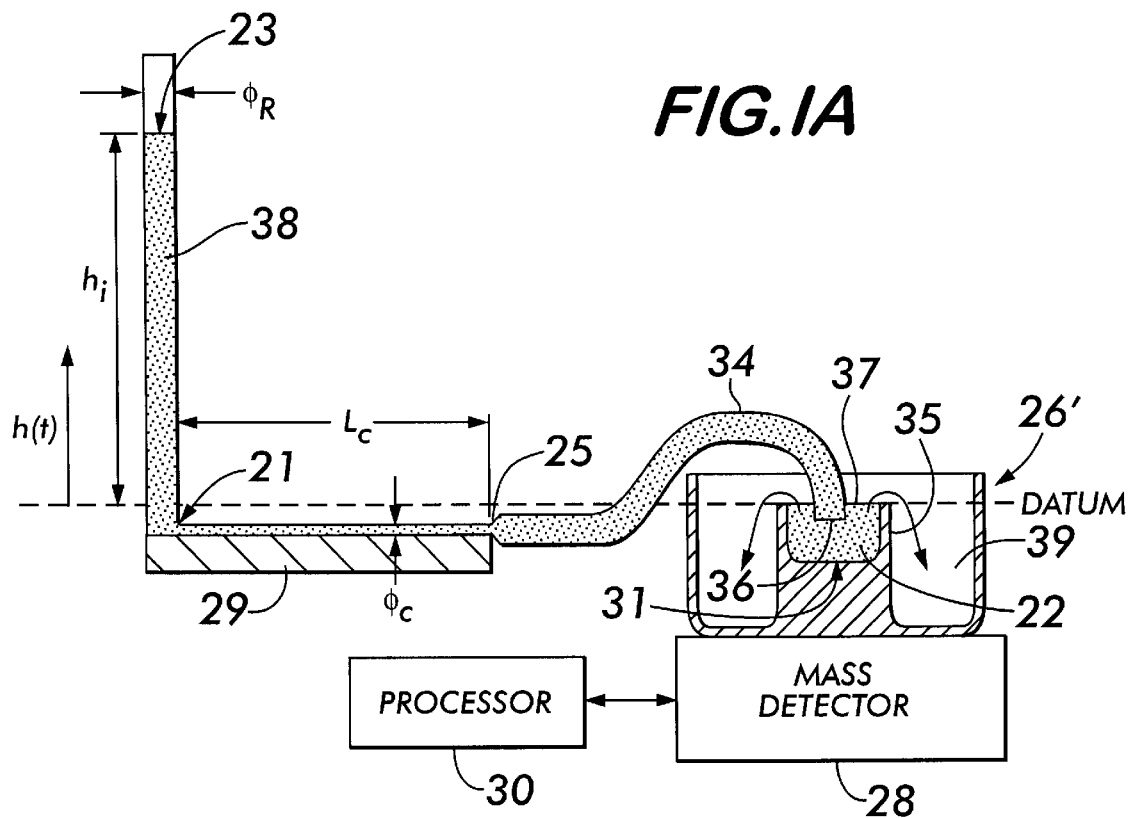
FIG. 1A is a functional diagram of the MDCV showing a fluid under test at the beginning of the viscosity test run and using a preferred fluid collector.
Figure 1B:
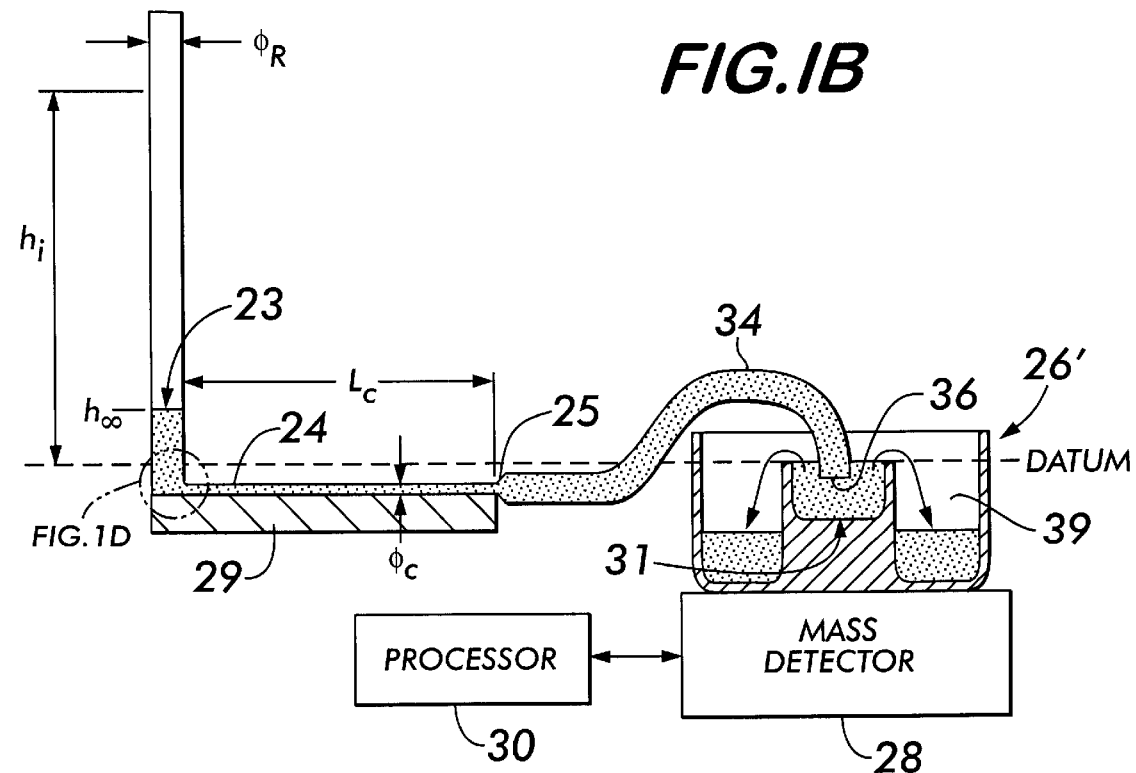
FIG. 1B is an enlarged partial view of an alternative fluid collector used in the MDCV.

It should be understood that although it is preferable to have the riser R in a vertical position, it is within the broadest scope of this invention to have the riser R oriented at any angle, greater than zero degrees, with respect to a horizontal reference (e.g., datum line shown in FIGS. 1A and 1B).

As will be discussed in detail later, test fluid 22 resides in the collector 26 from the start. An auxiliary suction source 32 is then coupled to the open top of the riser R. When the auxiliary suction source 32 is activated, the test fluid 22 is drawn up from the collector 26, through the capillary tube 24 and then up into the riser R to a desired level. The result is a continuous, non-moving sample of fluid that occupies the majority of the riser R (which forms a "column of fluid" 38, as discussed later) and the capillary tube 24; in addition, the only gas-liquid interface (23, see FIGS. 1A/1B) formed thereby is in the riser tube R. The auxiliary suction source 32 is then de-activated (e.g., vented to atmosphere) and the result is a falling column of the test fluid 22 through the riser R and through the capillary tube 24, and then into the collector 26. As will also be discussed in detail later, where the test fluid exhibits yield stress, $\tau_y$, a residual amount of the test fluid 22 remains in the riser R after a long period of time at the end of the test run; in addition, there are surface tension effects that also contribute to this residual amount of test fluid 22 as a result of the gas-liquid interface 23 (FIG. 1B). The height of this residual column of fluid is known as $\Delta h_\infty$, where $\Delta h = h(t) -$ datum level and where $h(t)$ represents the height of the column of test fluid in the riser R at any time; the term $h_\infty$ represents the final height of the column of test fluid in the riser R at the end of the test run after a long period of time. As will also be discussed later, the viscosity determination of the test fluid 22 can be determined using the MDCV 20 without the need to determine $h(t)$ or the initial position, $h_i$, of the test fluid 22 column in the riser R.

It should be understood that the datum line is the top edge of an inner wall 35 of a preferred collector 26'.

FIG. 1A depicts the MDCV 20 in further detail. In particular, the riser R and capillary tube 24 are supported on a base 29. The open end 25 of the capillary tube 24 can be integrally formed with an adaptor 34 which has an open end 36 that is submerged in a reservoir of test fluid 22 of a preferred collector 26'. It is preferable that the diameter of the adaptor 34 be similar to the diameter $\phi_R$ of the riser R.

It should be further understood that, although not shown, the riser R, the capillary tube 24 and the adaptor 34 are all temperature-controlled, i.e., these portions of the MDCV 20 are properly maintained at a desired temperature throughout the test run to minimize the effects of any temperature variation in the viscosity measurements. This is the case for all embodiments of the MDCV, and the CHDC viscometer 120, discussed throughout this Specification.

Figure 1C:
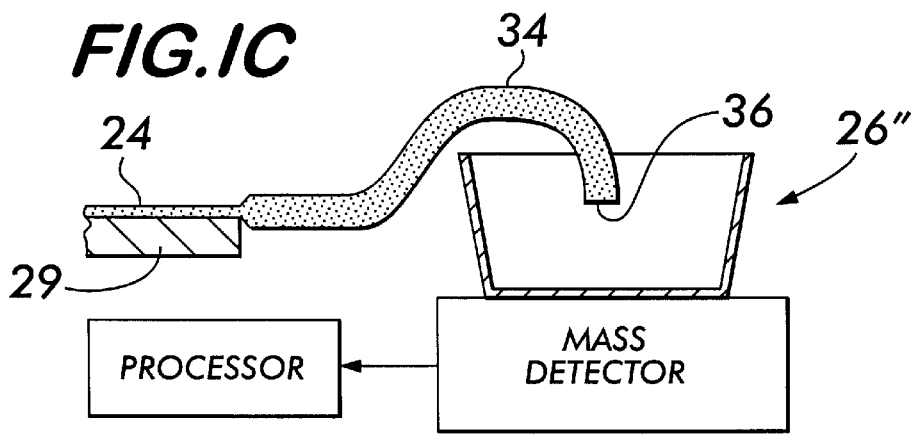
FIG. 1C is an enlarged view of an alternative fluid collector for use with the MDCV.
Figure 1D:
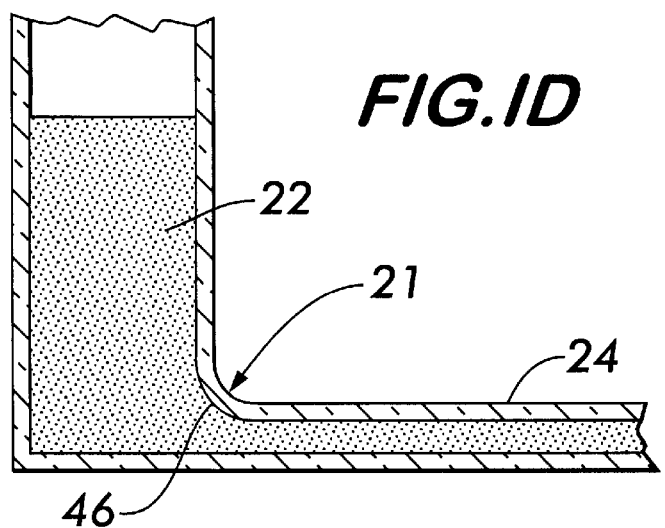
FIG. 1D is enlarged view of the elbow portion of the MDCV.
Figure 1E:
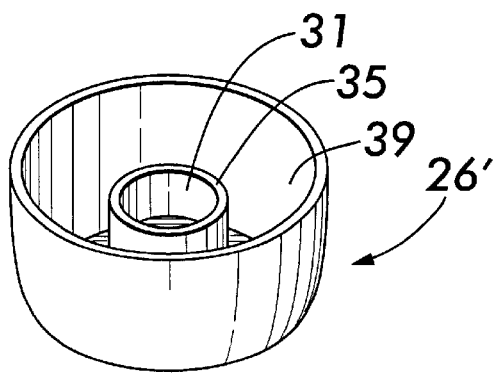
FIG. 1E is an isometric view of the preferred fluid collector used in the MDCV.

An isometric view of the preferred collector 26' is shown in FIG. 1E. The preferred collector 26' comprises an inner circular wall 35 that divides the collector 26' into a central portion 31 and an annular portion 39. The central portion 31 holds the original test fluid 22 sample therein. As mentioned earlier, when the auxiliary suction source 32 is coupled to the open top of the riser R and activated, the test fluid 22 is drawn out of the central portion 31, through the adaptor 34, through the capillary tube 24 and up the riser R to a desired height, $h_i$, to form a column of fluid 38. When the auxiliary suction source 32 is de-activated, the column of fluid 38 falls through the riser R, the capillary tube 24, the adaptor 34 and then into the central portion 31. Any overflow spills into the annular portion 39.

It should be understood that when the test fluid 22 is drawn out of the central portion 31 to form the column of fluid 38, the phrase "column of fluid 38" is meant to cover both the test fluid 22 that occupies the riser R as well as the test fluid 22 that occupies the capillary tube 24. Together these two components of test fluid 22 form a continuous (i.e., test fluid 22 only) sample of fluid. Initially, this sample of fluid is non-moving until the auxiliary suction source 32 is de-activated where this sample of fluid begins moving through the riser R and capillary tube 24. Thus, the phrase "column of fluid 38" references both the test fluid in the riser R and the capillary tube 24 when it is non-moving and when it is moving.

It should also be noted that the open end 36 of the adaptor 34 remains submerged under the fluid level in the central portion 31 during the test run to minimize any surface tension effects that would normally occur if the open end 36 was positioned above the fluid level in the central portion 31. In particular, as shown in FIGS. 11A–11D, the test fluid 22 is first deposited into the central portion 31 of the preferred collector 26' with any spillover 22' passing into the annular portion 39. Because the open end 36 of the adaptor 34 is submerged in the test fluid in the central portion 31, a finite amount of test fluid 22 wicks up into the transfer tube 34 and the capillary tube 24, as shown in FIG. 1A. Next, with the auxiliary suction source 32 (not shown in FIGS. 11A–11D) coupled to the top of the riser R and then activated, the test fluid 22 is drawn upward out of the central portion 31, through the adaptor 34, the capillary tube 24 and up into the riser R (not shown in FIGS. 11A–11D) to a form a column of fluid of a desired height; this movement is indicated by the arrows 40 in FIG. 11B. As can also be seen in FIG. 11B, the test fluid level in the central portion 31 has dropped. Before the column of fluid is permitted to flow downward, the fluid level in the central portion 31 must be raised to ensure that the open end 36 of the adaptor 34 remains submerged during the test run. Therefore, as shown in FIG. 11C, the spillover 22', or additional test fluid from another source (not shown), can be manually deposited in the central portion 31 using, for example, a syringe 42 in order to raise the level of the test fluid in the central portion 31. Finally, the column of test fluid 38 is then released using the auxiliary suction source 32 (as will be discussed later), wherein the column of test fluid 38 falls down the riser R, through the capillary tube 24, through the adaptor 34 (as shown by arrows 44) and into the central portion 31, with any spillover 22' passing into the annular portion 39. This occurs while the open end 36 of the adaptor 34 remains submerged in the test fluid of the central portion 31.

It should be understood that the datum line, mentioned previously, is selected as the top edge 37 (FIGS. 1A–1B) of the inner wall 35 of the preferred collector 26'.

It should also be understood that a less preferred embodiment for the collector 26 is shown in FIG. 1C where a standard collector 26" having no internal wall can be used; however, to minimize any surface tension effects, the open end 36 of the adaptor 34 should remain submerged in the test fluid (not shown) in the collector 26".

As shown most clearly in FIG. 1D, the upper bend 46 in the riser R/capillary tube 24 is rounded for minimizing any ΔP (change in pressure) at the inlet 21 to the capillary tube 24. This is the case for all embodiments of the MDCV discussed throughout this Specification. This is also the case for the single riser/single capillary viscometer 120 (FIG. 15A), as will also be discussed later.

Figures 2A, 2B:
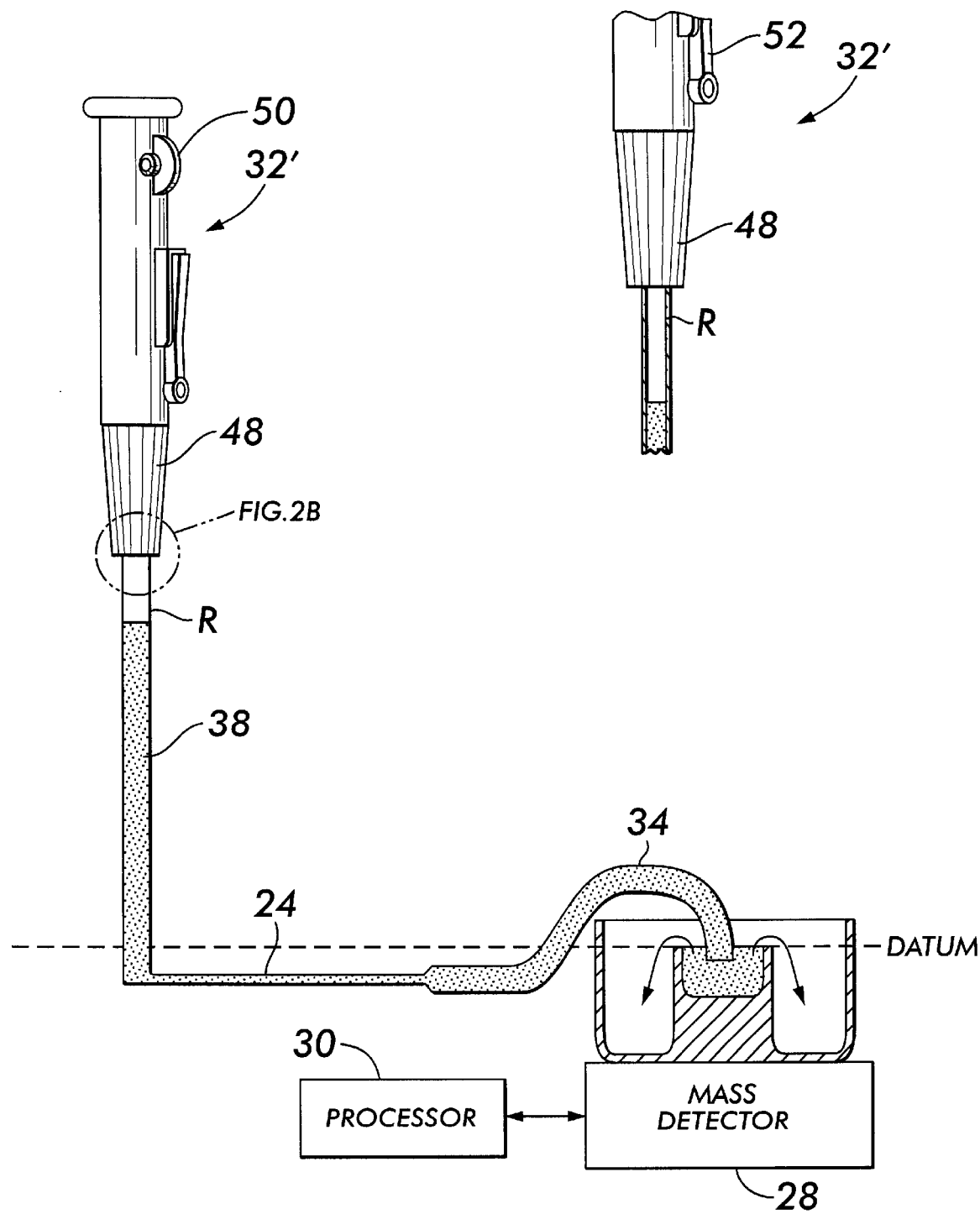
FIG. 2A shows a functional diagram of the MDCV of FIG. 1 including a particular auxiliary suction source for creating the initial column of test fluid for the viscosity test run.
FIG. 2B is an enlarged view of that portion of FIG. 2A indicated accordingly.

As shown in FIGS. 2A–2B, the auxiliary suction source 32 can be implemented using a dispensing mechanism such as the Cole-Parmer EW-06221-34: Pipette Pump with rapid-release lever 32'. In particular, the tip 48 of the pipette pump 32' is fitted over the top of the riser R as shown in FIG. 2B. The operator then rotates a rotary switch 50 that displaces an internal piston (not shown) which draws up the test fluid 22 from the collector 26' to form the column of fluid 38; when the desired height of the column of fluid 38 is achieved, $h_i$, the operator stops rotating the switch 50. As mentioned earlier, the operator must then re-fill the central portion 31 of the collector 26' to ensure that the open end 36 of the adaptor 34 remains submerged during the test run. The operator then depresses a rapid-release lever 52 that vents the pipette pump 32' to atmosphere, thereby allowing the column of fluid 38 to fall while the mass detector 28 detects the continuing mass increase being collected in the collector 26'.

Figure 2C:
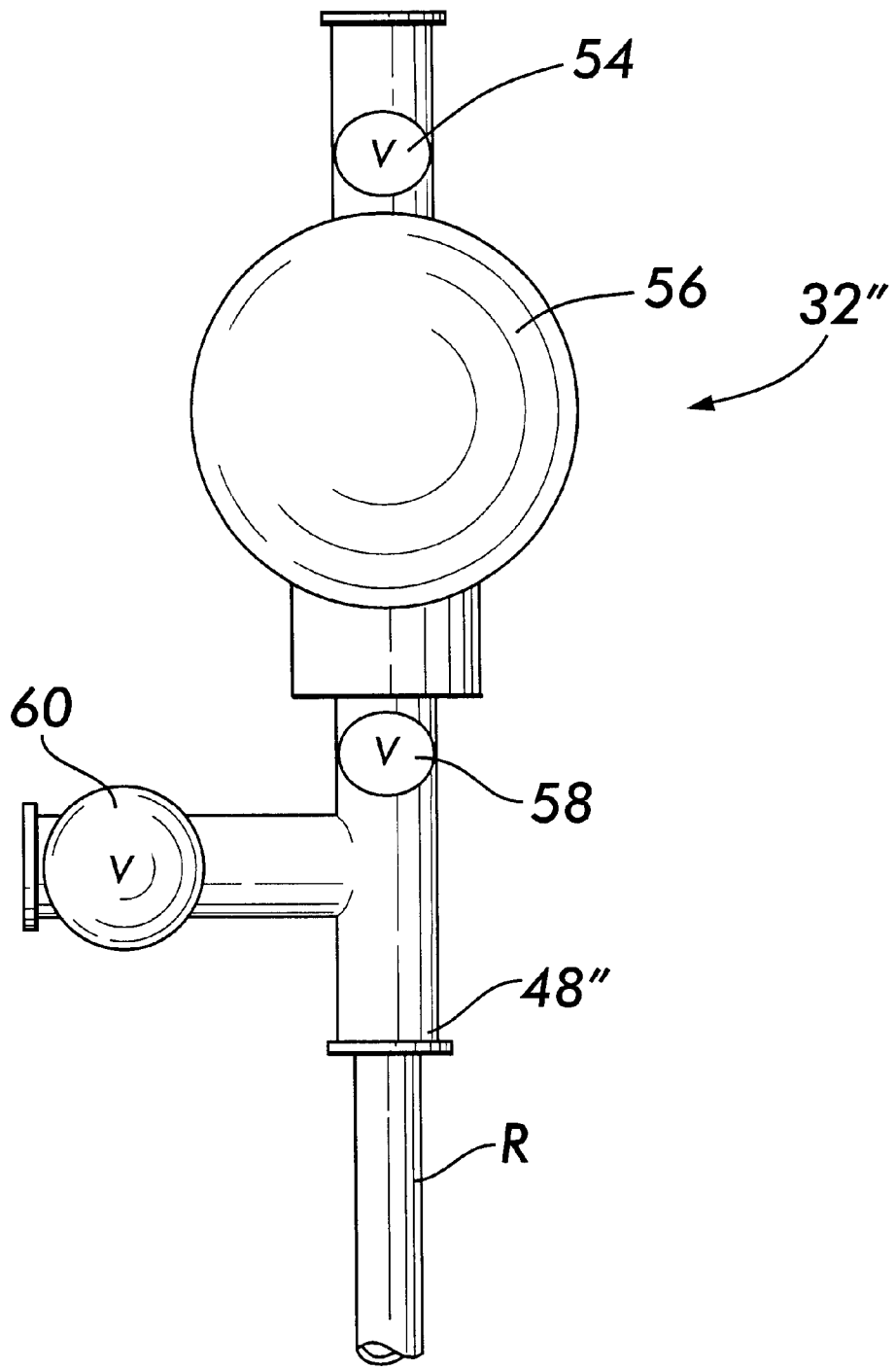
FIG. 2C is an enlarged view of an alternative auxiliary suction source for use with the MDCV.

Alternatively, the auxiliary suction source 32 can be implemented using a Cole-Parmer EW-24805-10 Pipette Filler 32", as shown in FIG. 2C. In particular, the tip 48" of the pipette pump 32" is fitted over the top of the riser R as shown in FIG. 2C. The operator then depresses a first valve switch 54 and then compresses a pliable bulb 56. These two actions provide a vacuum insider the pipette pump 32". When the operator then depresses a second valve switch 58, a suction pulls test fluid 22 up from the collector 26', as described previously for establishing the desired column of fluid height, $h_i$. The operator then re-fills the central portion 31 of the collector 26' to make certain that the open end 36 of the adaptor remains submerged during the test run. Next, the operator then depresses a third valve switch 60 which vents the pipette pump 32" to atmosphere, thereby allowing the column of fluid 38 to fall.

It should be understood that before operator permits the column of fluid 38 to fall, using the auxiliary suction source 32, the mass detector 28 makes an initial mass detection of the collector 26', including any test fluid 22 that is in the collector 26' prior to the release of the column of fluid 38.

Using the MDCV 20 described above, two Newtonian fluids (e.g., water, silicon oil—see FIGS. 3–5) were analyzed for viscosity and two non-Newtonian fluids (e.g., Separan 1000 ppm, blood—see FIGS. 6–7) were also analyzed. In particular, aqueous solutions of commercial polyacrylamide (Separan AP-273) and polyacrylic acid (Carbopol 934) were selected as test fluids because they are commonly used thickeners in the chemical industry and related fields. In the test runs discussed below, only one concentration of 1000 wppm solutions was tested. Separan AP-273 is a hydrolyzed Polyacrylamide, which shows anionic polymeric properties in aqueous solution with long chain linear structure of a basic unit connected by the strong hydrogen bonding. This polymer is produced as a white, free flowing, amorphous solid with an average molecular weight between $1 \times 10^4$ and $5 \times 10^6$. Carbopol 934 is a branched form of the polyacrylic acid polymers crossed-linked with allyl sucrose with an approximation of the molecular weight of $3 \times 10^6$. The pH value of the aqueous Carbopol solution is 2.7 to 3.5. However, with the addition of the alkali solution, such as sodium hydroxide, the rheology of the Carbopol solution changes dramatically. In the these tests, the Carbopol solution was neutralized. Both of the polymers were well-dissolved into distilled water. The detailed preparation of the test fluid was as follows: first, approximately half of the required amount of distilled water was poured into a beaker. A predetermined amount of polymer was then mixed with water, while the water was gently stirred with a paddle. Then, the remainder of the required water was added to the beaker. In order to make the homogeneous solutions, the solution was mechanically stirred at low speed. For Carbopol solutions, the test fluid was neutralized to increase its viscosity. As recommended by the manufacturer, a 10% sodium hydroxide solutions was used to neutralize the Carbopol solution. The sodium hydroxide solution was then added to the Carbopol solution by drop from a calibrated burette until the pH value of 7±0.2 was obtained. For Separan AP-273, neutralization was not required.

The viscosity results were compared against conventional viscometers, e.g., the Haake VT550 and the Physica RV (UDS-200). During the test runs, the capillary tube 24 comprised a diameter of 1.08 mm and a length of 20 mm. The mass detector 32 used comprised a precision balance that was used to measure the collected fluid mass variation m(t) and had a resolution of approximately 0.01 grams. The instantaneous mass of the collected fluid was recorded in a computer data file through an analog-to-digital data acquisition system that can be represented by the processor 30.

In particular, during operation, the column of fluid 38 was established in the riser R. At time t=0, the column of fluid 38 was permitted to fall such that test fluid 22 was allowed to flow through the capillary tube 24. Then, the test fluid 22 flowed through the capillary tube 24 and was collected in the collector 26. As the column of fluid 38 in the riser R decreased, the head difference through the capillary tube 24 continued decreasing. When the fluid level in the riser R approached the bottom of the riser R, the test fluid 22 stopped flowing. Typically, it took approximately 5 to 10 minutes for a fluid level in the riser R to reach an asymptote for water. The time to complete a test run should vary depending on the types of fluids and the size of the riser tube R. It should be noted that if a larger diameter riser tube R is used, a longer time for a run is required. For example, it took approximately 30 minutes for water with a 30 mm diameter riser tube R, but only 4 minutes with a 10 mm diameter riser tube R. However, the larger the diameter of the riser tube R, the more accurate the data.

Theory of Operation

Figure 8A:
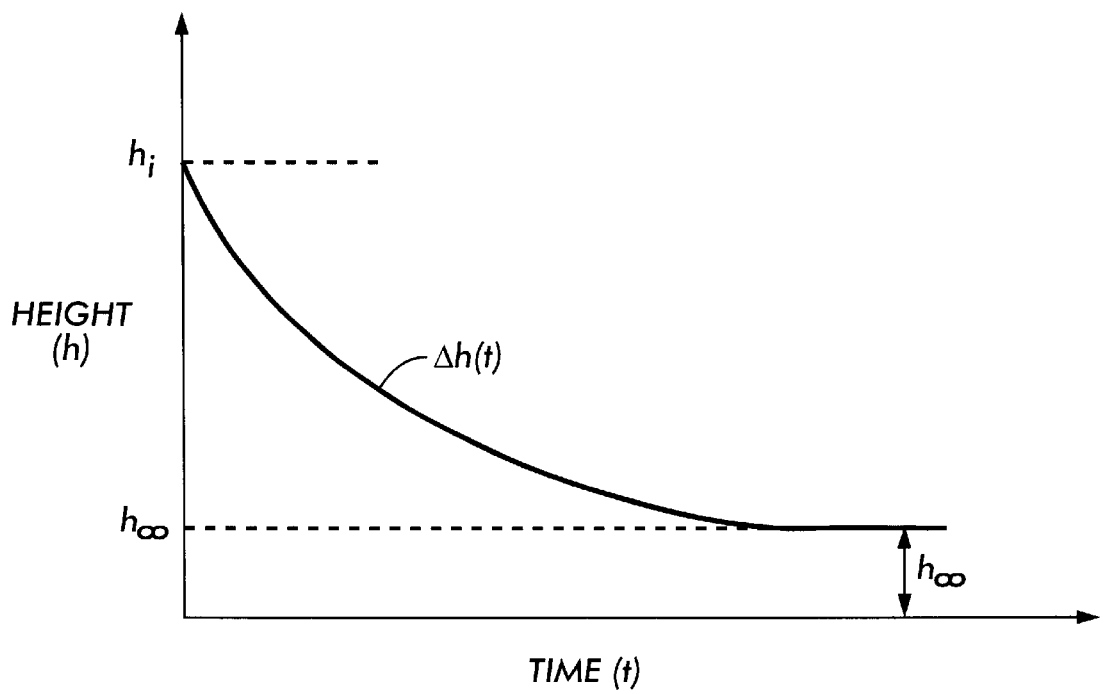
FIG. 8A shows a height vs. time plot of the test fluid in the MDCV.
Figure 8B:
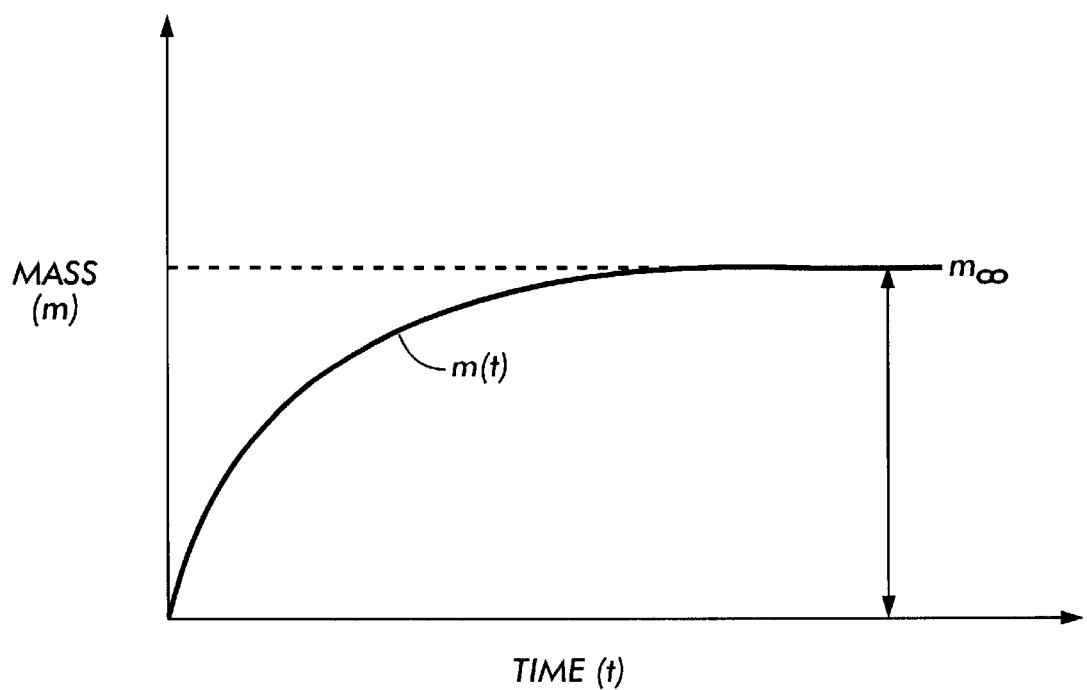
FIG. 8B shows a mass vs. time plot of the test fluid in the MDCV.

Using this configuration of riser R and capillary tube 24, the test fluid 22 is subjected to a decreasing pressure differential that moves the test fluid 22 through a plurality of shear rates (i.e., from a high shear rate at the beginning of the test run to a low shear rate at the end of the test run, as can be clearly seen in the column height change—FIG. 8A and the mass accumulating in the collector 26'—FIG. 8B), which is especially important in determining the viscosity of non-Newtonian fluids. In particular, once the desired height, $h_i$ is achieved by the column of fluid 38 and when the upper end of the riser R is exposed to atmospheric pressure, a pressure differential is created between the column of fluid 38 and the outlet 36 of the adaptor. As a result, the column of fluid 38 flows down the riser R, through the capillary tube 24, through the adaptor 34 and into the collector 26'. As the column of fluid 38 flows through these components, the movement of column of fluid 38 causes the pressure differential to decrease, thereby causing the movement of the column of fluid to slow down. This movement of the column of fluid 38, initially at a high shear rate and diminishing to a low shear rate, thus covers the plurality of shear rates. However, it should be understood that it is within the broadest scope of this invention to include any other configurations where the test fluid 22 can be subjected to a decreasing pressure differential in order to move the test fluid 22 through a plurality of shear rates.

The rate of flow through the capillary tube 24 is equal to the rate of change of the mass of the test fluid 22 collected on the mass detector 28. Hence, the corresponding flow rate in the capillary tube 24 can be expressed as:

$$Q(t) = \frac{1}{\rho} \frac{dm}{dt} \tag{1}$$

where $\rho$ is the density of the test fluid 22.

In order to determine the viscosity of the test fluid 22, it is necessary to know the pressure drop across the capillary tube 24. What was measured using the MDCV 20 was the total pressure drop between the riser R and the capillary tube outlet 25 including not only the pressure drop across the capillary tube ($\Delta P_c$) but also the pressure drop occurring at the inlet 21 and outlet 25 ($\Delta P_e$). One of the accurate methods for determining ($\Delta P_e$) is to make a Bagley plot (see C. W. Macosko, *Rheology: Principles, Measurements, and Applications* (VCH, 1993)) with at least two short capillary tubes (not shown) of the same diameter. Hence, the pressure drop occurring at the inlet 21 and at the outlet 25 of the capillary tube 24 had to be subtracted from the total pressure difference ($\Delta P_t$). Considering these pressure drops, the pressure drop across the capillary tube 24 can be described as $$\Delta P_c = \Delta P_t - \Delta P_e \tag{2}$$

It should be noted that the contribution from the second term on the right hand side ($\Delta P_e$) in Eq. (2) is less than 0.5%; hence this term can be neglected for all practical purposes, and as a result, equation 2 reduces to:

$$\Delta P_c \Delta P_t \tag{3}$$

An expression, therefore, for the total pressure as well as the pressure across the capillary tube 24 is:

$$\Delta P_t = \Delta P_c = \rho g[h_i - \Delta h(t) - h_\infty] = \rho g[h_i - h_\infty - \Delta h(t)] \tag{4}$$

where $\Delta h(t)$ represents the changing height of the falling column of fluid 38 and is given by the following equation:

$$\Delta h(t) = \frac{4m(t)}{\rho \pi \phi_R^2} \tag{5}$$

and where:
  $h_i$ is the initial height of the column of fluid 38;
  $h_\infty$ is the final height of the column of fluid 38 after a long period of time;
  m(t) is the mass of the collector 26 over time; and
  $\phi_R$=diameter of the riser tube R.

In addition, the final mass after a long period of time, $m_\infty$, can be expressed in terms of the height of the column of fluid 38 as follows:

$$m_\infty - m_i = \rho \left(\frac{\pi \phi_R^2}{4}\right)(h_i - h_\infty); \tag{6}$$

and solving equation 6 for ($h_i - h_\infty$), $$(h_i - h_\infty) = \frac{4(m_\infty - m_i)}{\rho \pi \phi_R^2} \tag{7}$$

Thus, making the substitution of equations 5 and 7 into equation 4, $$\Delta P_c = \rho g \left[\frac{4(m_\infty - m_i)}{\rho \pi \phi_R^2} - \frac{4m(t)}{\rho \pi \phi_R^2}\right] = \frac{4g}{\pi \phi_R^2}[m_\infty - m_i - m(t)] \tag{8}$$

It is assumed that any surface tension effects are constant with time and throughout the test run, e.g., the surface tension experienced at $h_i$ is similar to the surface tension effect experienced at $h_\infty$.

The significance of equation 8 includes, among other things, that in order to determine the pressure across the capillary tube 24, only the difference between the final mass ($m_\infty$) and the initial mass ($m_i$), the diameter of the riser R and the mass data detected by the mass detector 28, m(t), need be known; the initial height of the fluid column 38, $h_i$, nor the final height, $h_\infty$ need to be known. Furthermore, equation 8 also represents, in accordance with the assumption that the surface tension is constant, a surface tension-free capillary 20.

Using the MDCV with Newtonian fluids

By assuming that the Hagen-Poiseuille law is applicable (see C. V. Easwaran and S. L. Kokal, SIAM J. Appl. Math., 52, 1501, (1992)), the rate of flow through the capillary tube 24 is given by:

$$Q(t) = \frac{\pi \Delta P \phi_c^4}{128 \mu L_c} \tag{9}$$

where $\phi_c$ is the diameter of the capillary tube 24, $L_c$ is the length of the capillary tube 24, Q is the volumetric flow rate, and $\mu$ is the viscosity of the test fluid 22.

Figure 4:
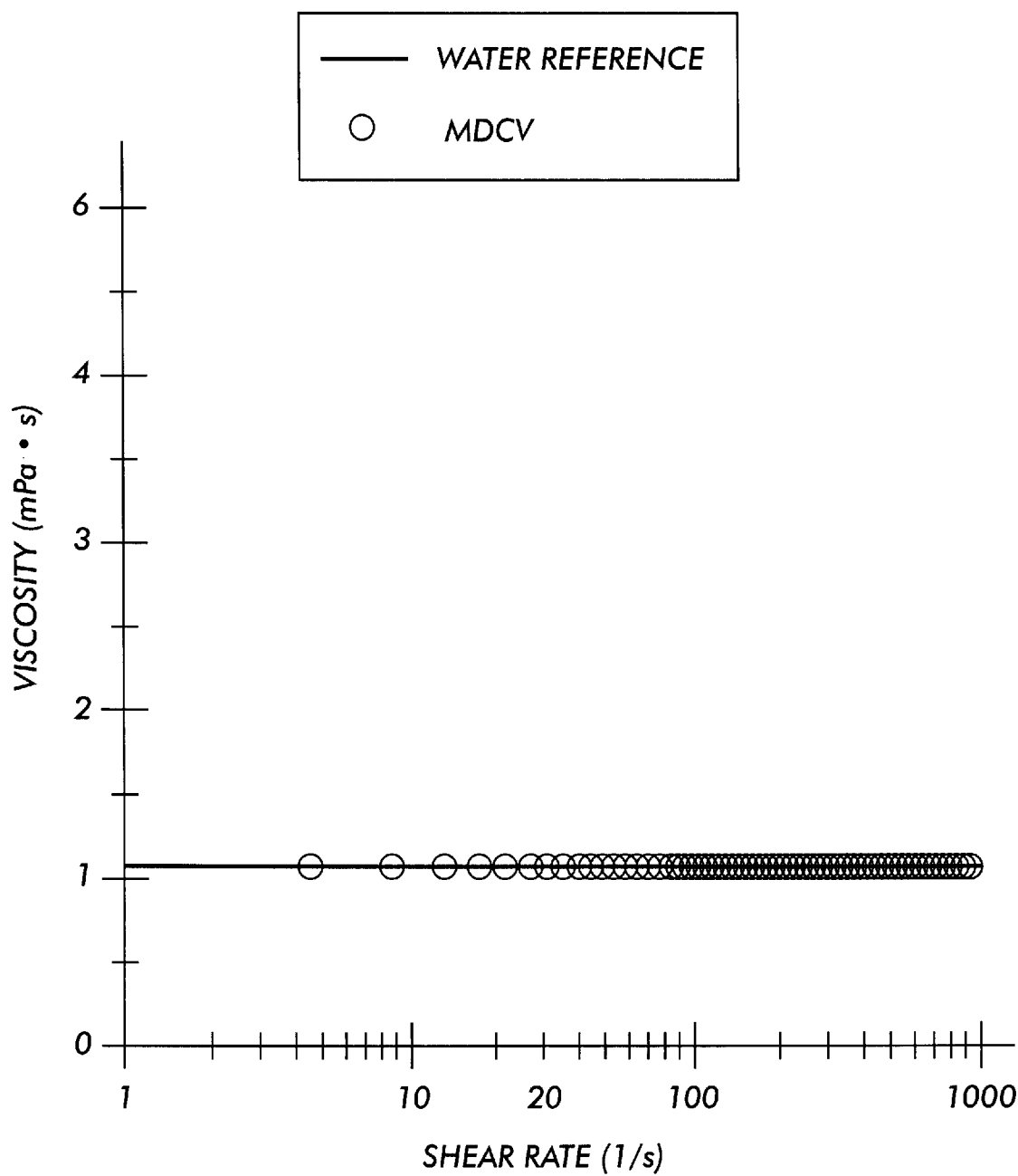
FIG. 4 shows the viscosity measurement for water at 18° C. using the MDCV as compared to the known water viscosity reference.
Figure 5:
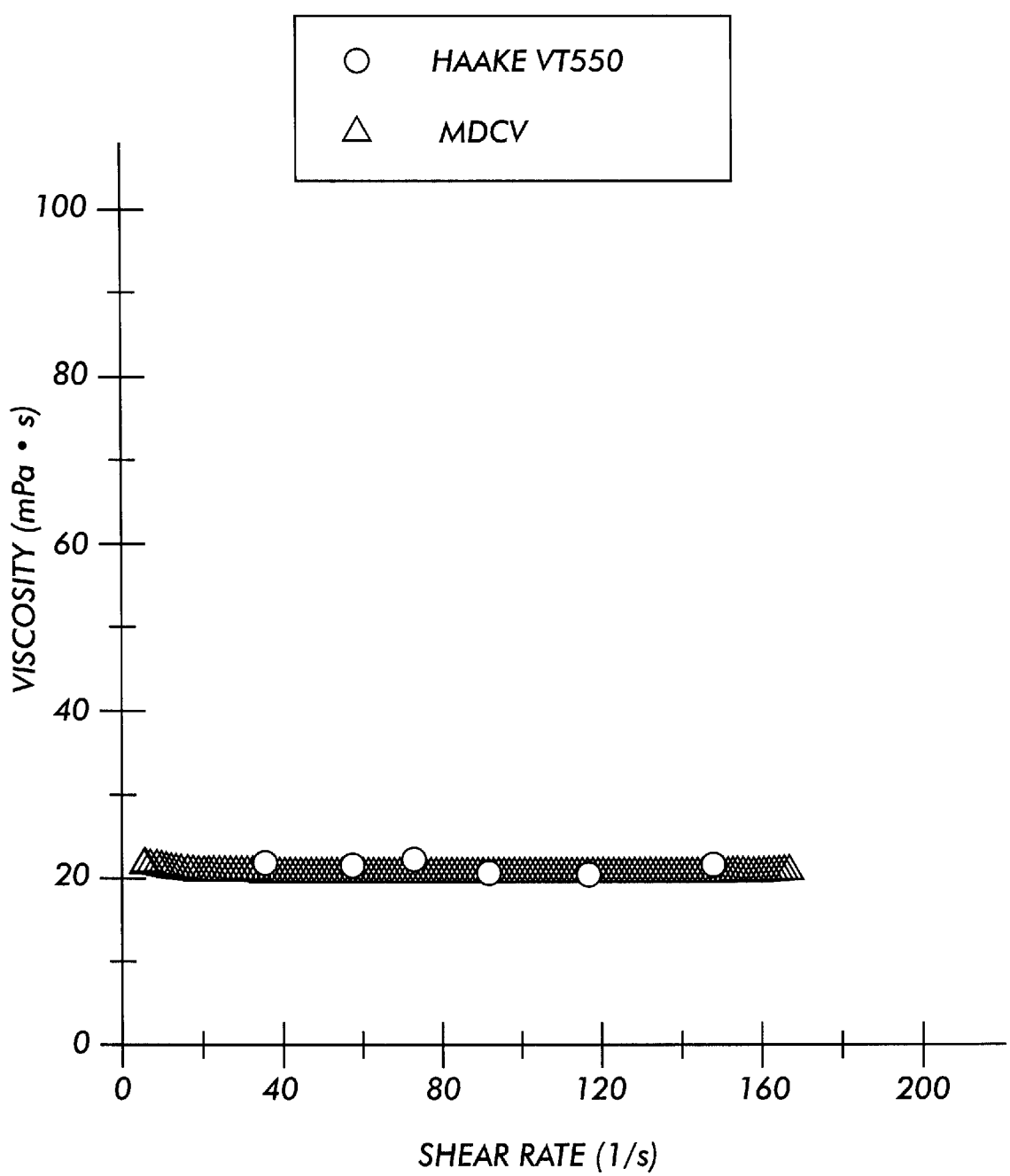
FIG. 5 shows the viscosity measurement for silicon oil (a Newtonian fluid) using the MDCV as compared to a conventional viscosity measuring device, namely, the Haake VT550.

Subsequently, the shear rates and the shear stress at the capillary tube 24 wall and viscosity were determined for Newtonian fluid as shown in FIGS. 4–5 (see C. W. Masko reference and C. V. Easwaran and S. L. Kokal, SIAM J. Appl. Math., 52, 1501 (1992)):

$$\dot{\gamma}_w(t) = \frac{32Q}{\pi \phi_c^3} = \frac{32}{\pi \rho \phi_c^3} \frac{dm(t)}{dt} \quad (10)$$

$$\tau_w(t) = \frac{\Delta P \phi_c}{4 L_c} = \frac{g \phi_c}{\pi \phi_R^2 L_c}[m_\infty - m_i - m(t)] \quad (11)$$

$$\mu = \frac{\pi \phi_c^4}{128 L_c} \frac{\Delta P}{Q} = \frac{\rho g \phi_c^4}{32 \phi_R^2 L_c} \left( \frac{m_\infty - m_i - m(t)}{\frac{dm(t)}{dt}} \right) \quad (12)$$

Non-Newtonian Fluids

The shear rate dependent viscosity for a non-Newtonian fluid flowing in the capillary tube 24 is obtained from experimental data with some mathematical treatment, and the necessary equations can be found in any standard handbook (e.g., C. W. Macosko). The shear rate at the capillary tube 24 wall is obtained form the classical Weissenberg-Rabinowitsch equation (see S. L. Kokal, B. Habibi, and B. B. Maini, Novel Capillary Pulse Viscometer for non-Newtonian Fluids, Review of Scientific Instrument, 67(9), pp. 3149–3157 (1996)):

$$\dot{\gamma}_w(t) = -\frac{dV_z}{dr}\bigg|_{r=R} \quad (13)$$

$$= \frac{1}{4}\dot{\gamma}_{aw}\left[3 + \frac{d\ln Q}{d\ln\tau_w}\right]$$

where $\dot{\gamma}_{aw}$ is the apparent or Newtonian shear rate at the wall and where $\phi_c$ is the diameter of the capillary tube 24.

$$\dot{\gamma}_{aw}(t) = \frac{32 Q(t)}{\pi \phi_c^3} \quad (14)$$

and the shear stress at the wall is given by:

$$\tau_w(t) = \frac{\Delta P(t) \phi_c}{4 L_c} \quad (15)$$

Thus, the viscosity corresponding to the wall shear rate is calculated in the form of a generalized Newtonian viscosity:

$$\eta = \frac{\tau_w}{\dot{\gamma}_w} = \frac{\pi \phi_c^4 \Delta P}{32 Q L_c}\left(3 + \frac{d\ln Q}{d\ln\tau_w}\right)^{-1} \quad (16)$$

$$= \frac{\rho g \phi_c^4 [m_\infty - m_i - m(t)]}{8 L_c \phi_R^2 \left(\frac{dm}{dt}\right)\left(3 + \frac{1}{n'}\right)}$$

where $$\frac{1}{n'} = \frac{d\ln Q}{d\ln\tau_w}.$$

Thus, Equation 11 represents the mass measured by the MDCV 20.

The viscosity versus shear rate information can be obtained from equations 13–16 by measuring the mass of the collected fluid with respect to the time from which the pressure drop and flow rate can be calculated. The values of R and L, must be obtained by calibration. Since equation (13) is non-linear, the procedure to calculate the shear rate and the corresponding viscosity is not straightforward. One of the approaches to obtain the viscosity from the general equations presented above is to adopt a finite difference technique for differentiation of equation (13). If there is enough data near the point of interest, it is possible to evaluate the derivative as:

$$\frac{1}{n'} = \frac{d\ln Q}{d\ln\tau_w} = \frac{1}{n} \quad (17)$$

where n is simply the exponent of the power law constitutive equation. Even though the power-law exponent is used in the above equations, this does not limit the capability of the present measurement for power-law fluids. The rigorous approach can still be taken for obtaining a viscosity versus shear rate relationship for any fluid (see S. L. Kokal, B. Habibi, and B. B. Maini, "Novel Capillary Pulse Viscometer for non-Newtonian fluids, Review of Scientific Instrument, 67(9), 3149–3157 (1996)).

Figure 3:
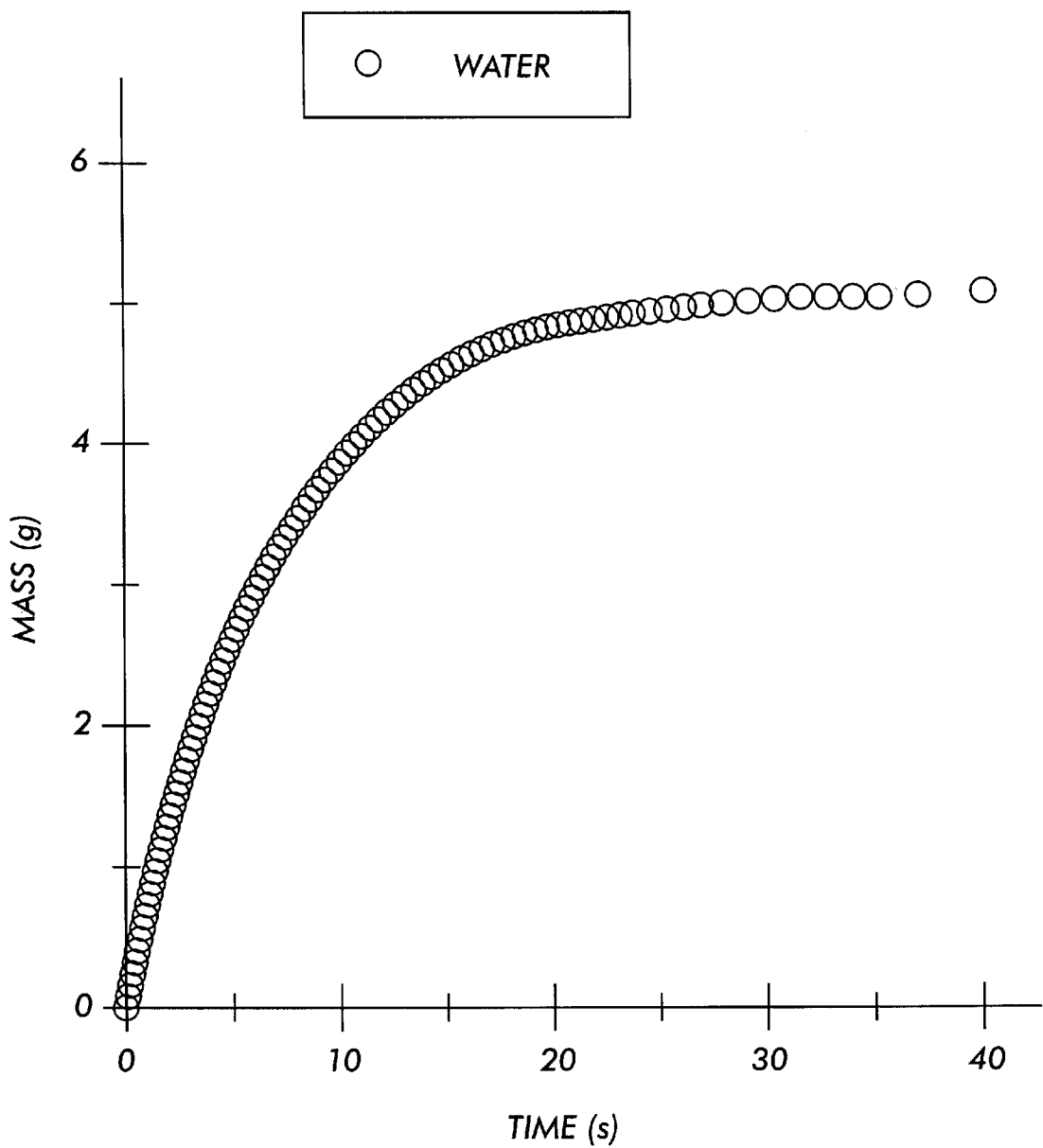
FIG. 3 shows mass variations obtained for the viscosity measurement for water at 18° C. using the MDCV.

FIGS. 3 and 4 show the test results obtained with water at room temperature. In particular, FIG. 3 shows the mass variation of the collected fluid m(t). As time passed, the collected fluid mass reached $m_\infty$ asymptotically. It should be noted that the rate of the collected mass increase decreased with time. This was caused by the decrease of the fluid level of the column of fluid 38 in the riser R that was the driving pressure head, subsequently resulting in the variation of volume flow rate with time. The viscosity of water was calculated from m(t) using equation 12.

FIG. 4 shows water viscosity at room temperature (at 18° C.) measured with the MDCV 20, rendering an average value of 1.09 mPa·s in a shear rate range between 5 and 1000 s$^{-1}$. The viscosity data for water in the literature (see C. V. Easwaran, et al.) is 1.07 mPa·s. Comparing it with the measured data using MDCV 20, the present test results yield approximately 1.8% error in a shear rate range between 5 and 1000 s$^{-1}$.

FIG. 5 shows the test results of another Newtonian fluid, silicon oil, using the MDCV 20 as compared to viscosity results from a conventional viscometer, namely, the Haake VT550.

Figure 6:
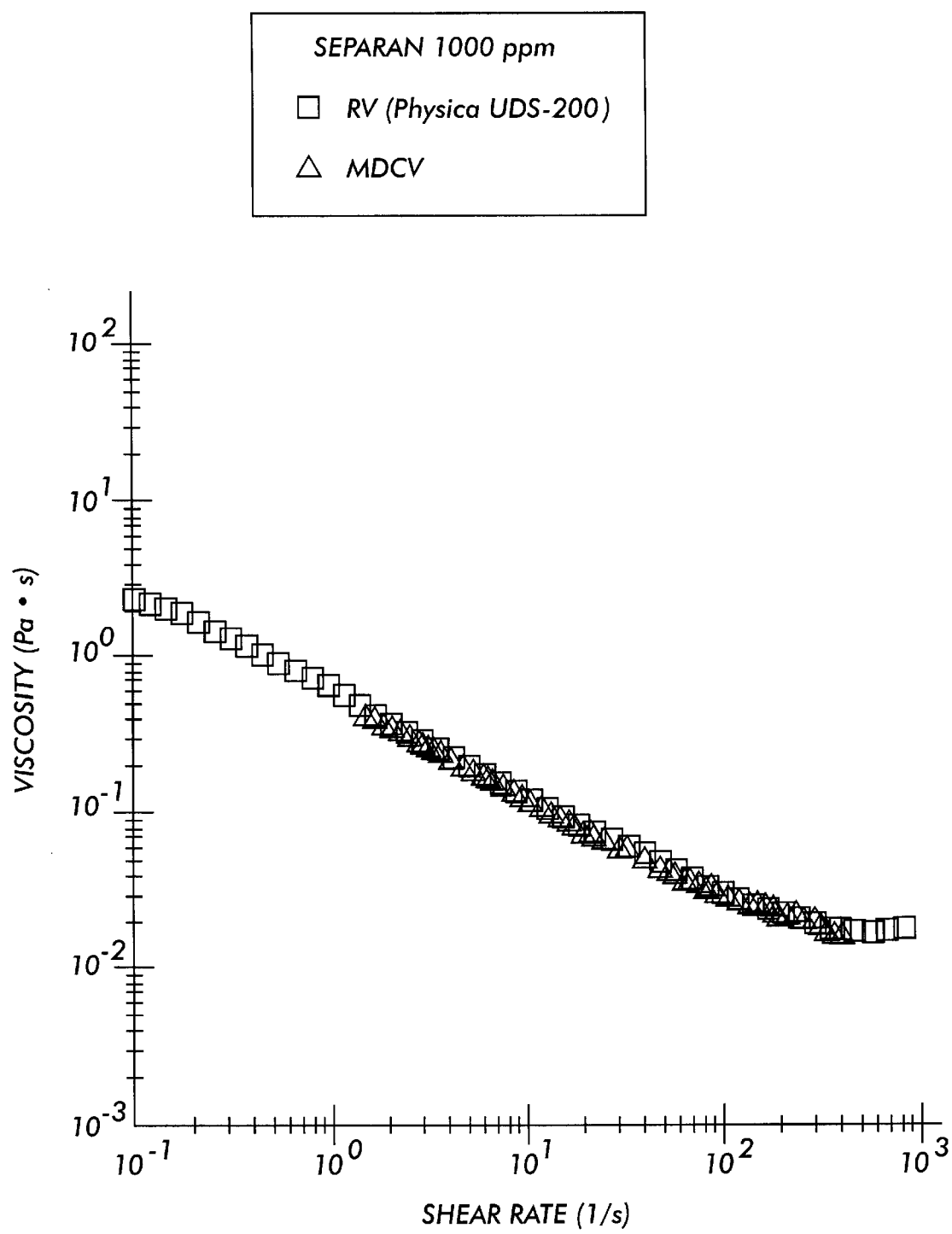
FIG. 6 shows a viscosity measurement (log—log scale) for Separin solution 1000 ppm using the MDCV as compared to another conventional viscosity measuring device, namely, the Physica RV UDS-200.

FIG. 6 illustrates the results for an aqueous polyacrylamide solution (1000 wppm). Although not shown, the mass variation, m(t), using the polyacrylamide solution (1000 wppm) exhibited similar results for as that for water (see FIG. 3). In particular, initially, the collected mass increased rapidly. As time passed, the rate of the collected mass decreased. Finally, the collected mass reached a plateau value, $m_\infty$, asymptotically. It should be noted that the longer the test time took, the lower the shear rate that could be obtained. FIG. 6 shows the viscosity results for the aqueous polyacrylamide solution at room temperature. For comparison, the test fluid viscosity was also measured by the rotating type viscometer (Physica-UDS 200). The open square symbol indicates the viscosity data measured with the rotating viscometer, whereas the open triangle symbol indicates those measured with the MDCV 20. In FIG. 6, the present results with MDCV 20 show an excellent agreement with those from the commercial viscometer over a range of shear rate ($10^0 \sim 10^3$ 1/s), including the low shear rate regime.

Figure 7:
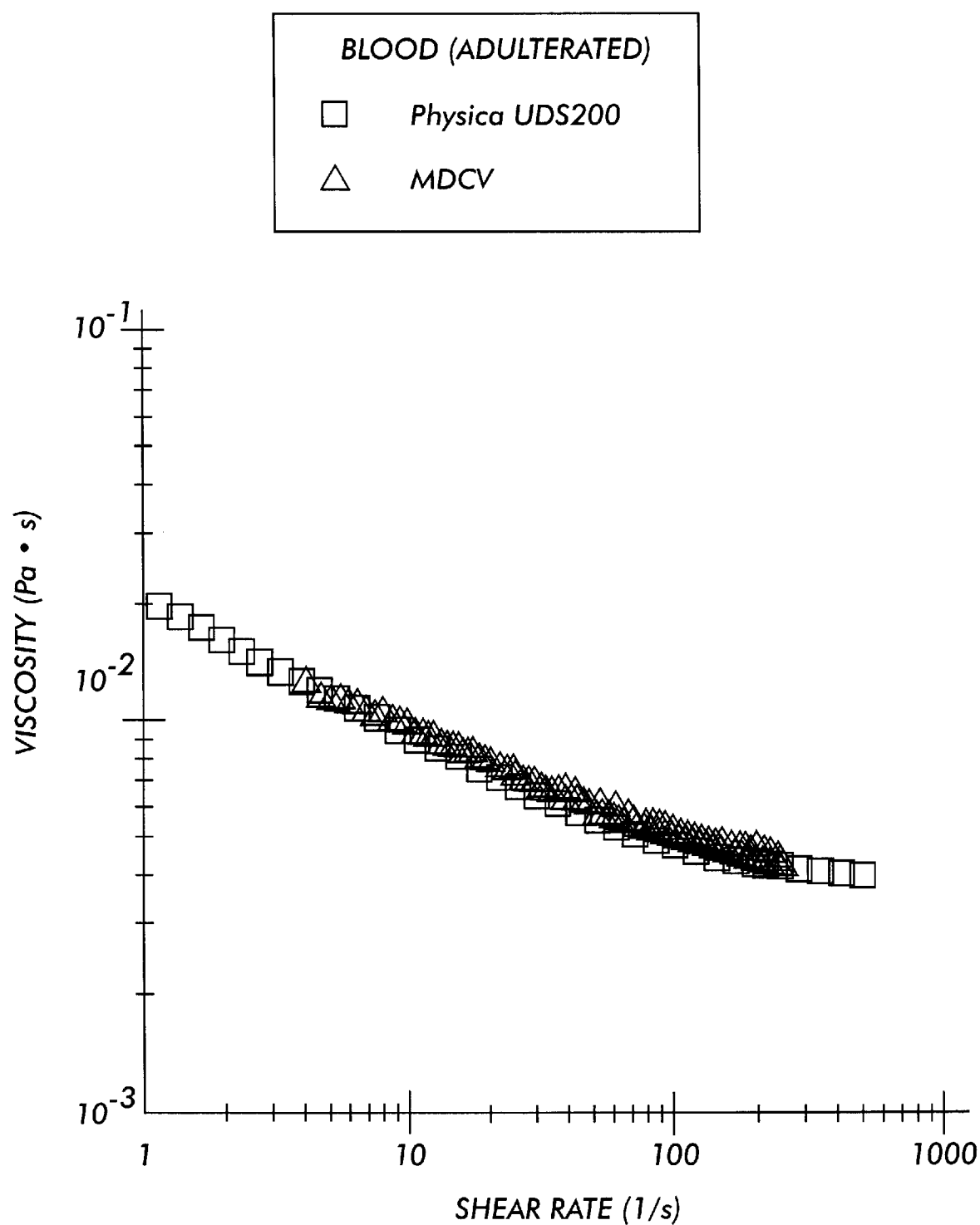
FIG. 7 shows a viscosity measurement (log—log scale) for blood using the MDCV as compared to the Physica RV UDS-200.

FIG. 7 illustrates the viscosity results for another non-Newtonian fluid, blood. The square symbol indicates the viscosity data measured with a conventional rotating viscometer (Physica-UDS 200), while the triangle symbol indicates those measured with the MDCV 20. The present results for the blood sample with the MDCV 20 show an excellent agreement with those from the UDS-200 over a range of shear rates.

FIGS. 8A and 8B provide a summary of the height vs. time characteristic of the falling column of fluid 38 during the test run. As can be seen in FIG. 8A, the level of the column of fluid 38 initially is at $h_i$. During the test run, the column of fluid 38 falls and arrives at a final column height of $h_\infty$ after a long period of time (e.g., 2–5 minutes after the column of fluid 38 begins to fall). As also mentioned earlier, this final height $h_\infty$ can be attributed to both the surface tension effect of the gas-liquid interface 23 (FIG. 1B) as well as any yield stress, $\tau_y$, exhibited by the test fluid 22. With regard to the change in mass, m(t), as shown in FIG. 8B, the mass climbs quickly and then slows down towards a final mass value, $m_\infty$ after a long period of time. As mentioned earlier, what is important here is that the viscosity of the test fluid 22 can be determined using the MDCV 20 without the need to know $h_i$ and $h_\infty$.

Figure 9:
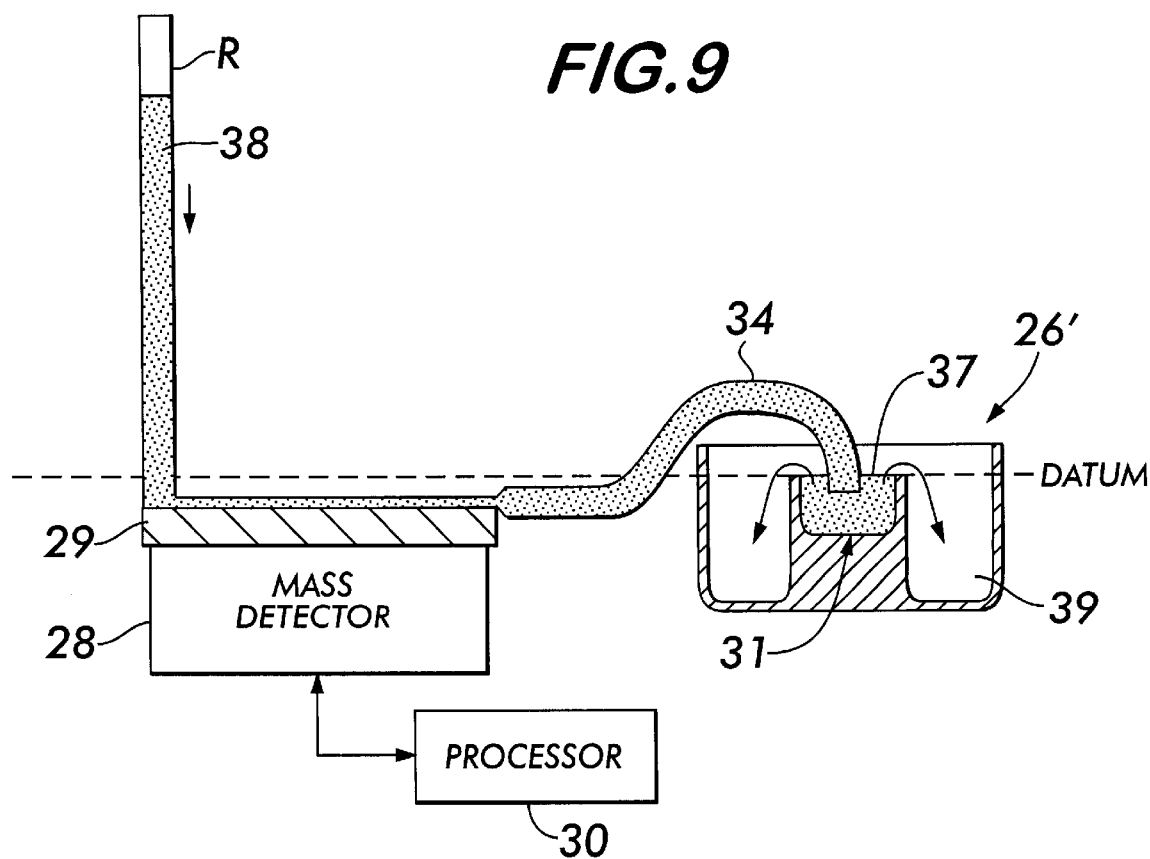
FIG. 9 depicts a second embodiment of the MDCV wherein the changing mass of the falling column is detected.
Figure 10:
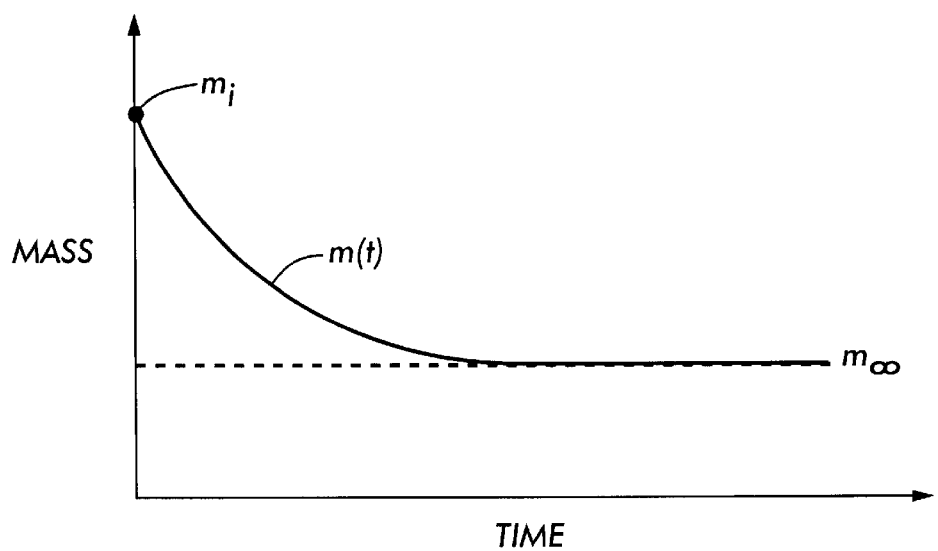
FIG. 10 depicts the mass vs. time plot for the test fluid using the second MDCV.

FIG. 9 depicts an alternative embodiment to the MDCV 20' wherein the changing mass of the riser R and capillary tube 24 are detected, rather than detecting the change in mass of the test fluid 22 collected in the collector 26'. Thus, rather than obtaining an increasing mass with time, the mass detector 32 detects the decreasing mass of the riser R/capillary tube 24 assembly with time, as shown in FIG. 10. The empty weight of the riser R, capillary tube 24 and the base 29 are taken into account before the test run is conducted. As a result, the expression for the pressure drop across the capillary tube 24 is:

$$\Delta P_c = \frac{4g}{\pi \phi_R^2}[(m_i - m_\infty) - m(t)]. \tag{18}$$

Other than that, the theory of operation of the MDCV 20' is similar to that discussed above with regard to the MDCV 20.

Figure 12A:
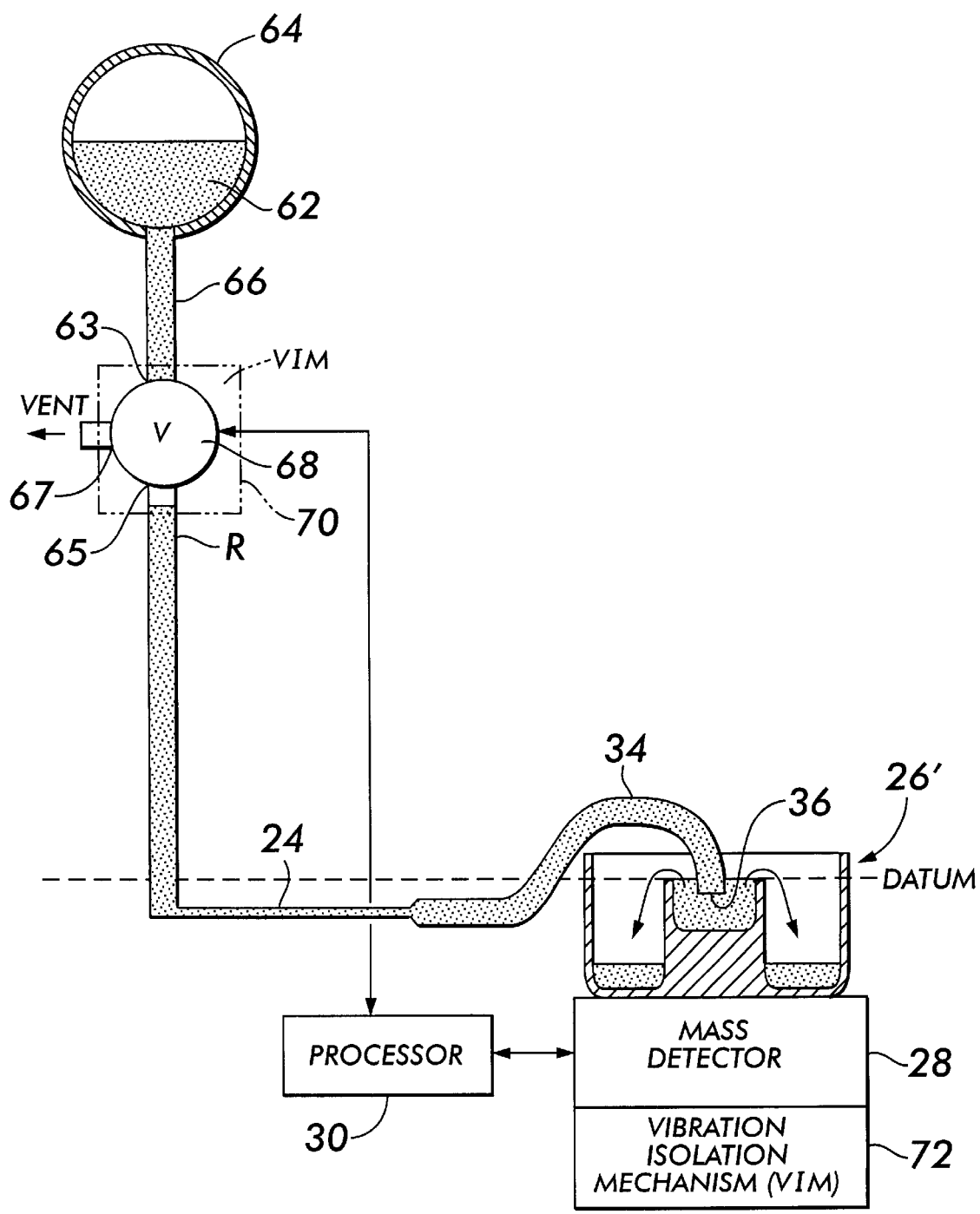
FIG. 12A depicts a functional diagram of an online MDCV.

FIG. 12A depicts an online use for the MDCV 20 in an industrial application. For example, given a flow of an industrial fluid 62 (e.g., polymer melt, paint, cosmetic, etc.) through a conduit 64, a tap-off plenum 66 permits a sample of the industrial fluid to be tested for viscosity online. In particular, a 3-way valve 68 is coupled between the tap-off plenum 66 and the top of the riser R. Furthermore, both the valve 68 and the mass detector are vibration-isolated from the industrial process via respective vibration-isolation mechanisms 70 and 72; this minimizes any vibratory effects that could corrupt the viscosity determination during the test run; such vibration-isolation mechanisms are known in the art and are not detailed any further in this application. The valve 68 may be controlled by the processor 30. For example, at a predetermined time, the processor 30 controls the valve 68 to permit a sample of the industrial fluid to enter the tap-off plenum 66, such as connecting a first port valve 63 to a second port valve 65 to not only form the column of fluid 38 but to also fill the collector 26' with a sufficient amount of the fluid to keep the outlet 36 of the adaptor 34 submerged. Next, the processor 30 further controls the valve 68 (e.g., by venting to atmosphere, such as connecting the second port valve 65 to a third port valve 67 exposed to atmosphere) to generate the falling column 38 of industrial fluid. Thus, via the use of this MDCV 20, as shown in FIG. 12A, the viscosity of an industrial fluid can be obtained online without disrupting the process.

FIG. 12B depicts another online MDCV application to the industrial process that detects the changing mass of the riser R and capillary tube 24, discussed previously, rather than the increasing mass of the fluid collector 26'. Also, various output means 73, e.g., a display 74, a printer 76, or a datalogger 78 are shown coupled to the processor 30 for conveying the viscosity results to an operator.

Where the changing mass of the riser R is detected, rather than the changing mass of the fluid collector 26', an example of the interface between the riser R and the mass detector 32 are shown in FIGS. 12C and 12D. In FIG. 12C, the mass detector 32 comprises a load cell 80 positioned on the VIM 72 which are positioned on the base 29. The extreme end 82 of the riser R is open such that the column of fluid 38 rests directly on a contact surface 84 of the load cell 80 and is termed "flush-mounted". To make sure no leaking occurs, a seal 86 seals the riser R/load cell 80 interface. Alternatively, as shown in FIG. 12D, a pliable membrane 88 can be used to close off the extreme end 82 of the riser R and wherein this flexible membrane 88 also forms a leak-proof seal. The membrane 88 supports the column of fluid 38 and is in direct contact with the load cell 80.

Figure 13:
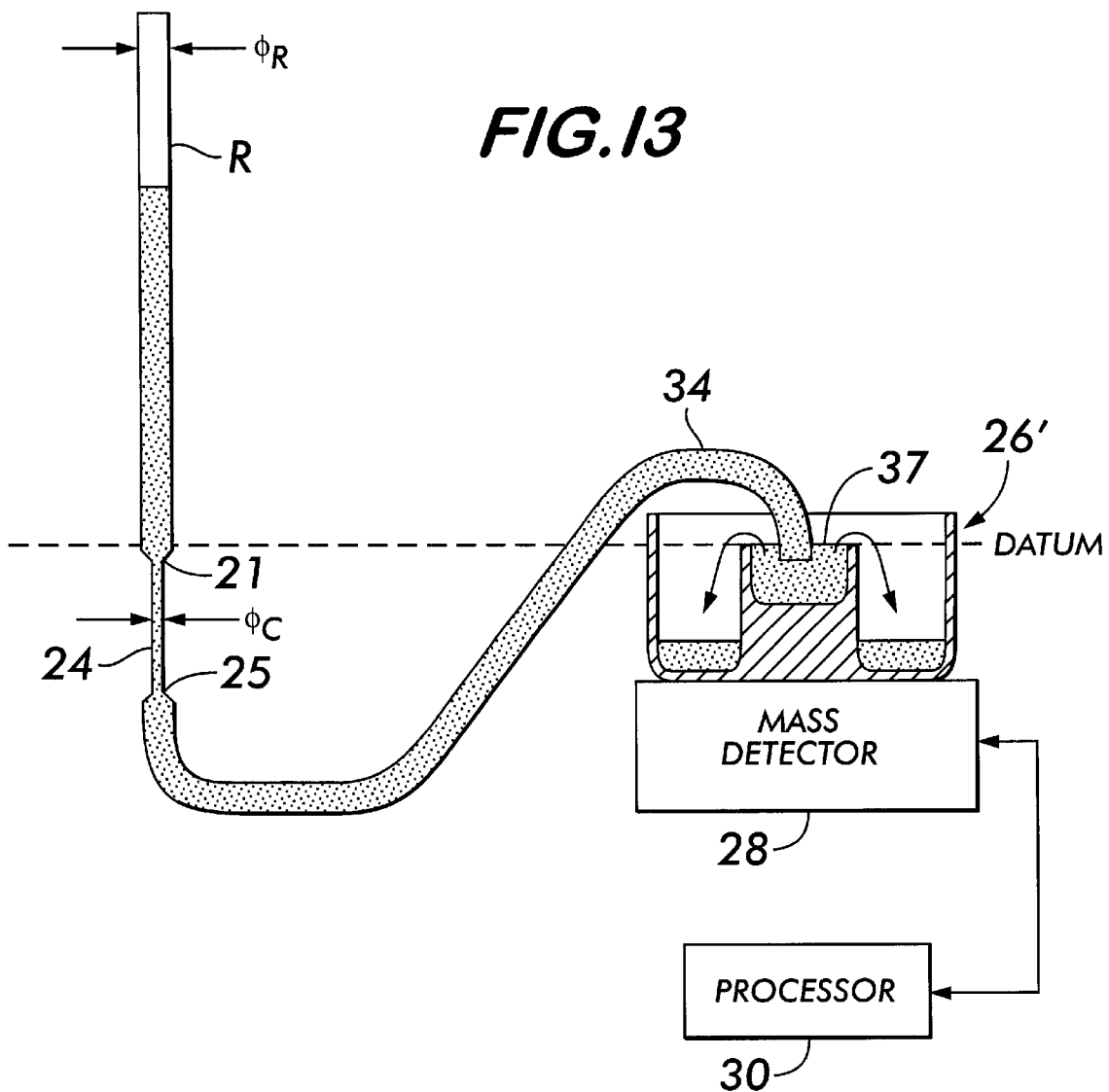
FIG. 13 depicts a third embodiment of the MDCV.

FIG. 13 depicts a third embodiment of the MDCV wherein the capillary tube 24 is vertically-oriented. For proper operation, the datum line needs to be above the inlet 21 of the capillary tube 24, as shown in FIG. 13. Other than that, the operation of this embodiment is governed by the same equations mentioned previously.

Furthermore, the present invention also includes a method for the online determination of the homogeneity of one or more components of a mixture in a fluid using the MDCV 20. In particular, by statistically analyzing the m(t) data as it is collected by the mass detector 32, an indicator of the homogeneity (i.e., how well mixed these components are) of a fluid mixture can be obtained. Although U.S. Pat. Nos. 4,733,684 (Marrelli) and 5,946,088 (Aldridge) disclose methods for also determining the homogeneity of a fluid, these methods are complex and do not teach nor suggest the mass analysis discussed in the present application.

Figure 14A:
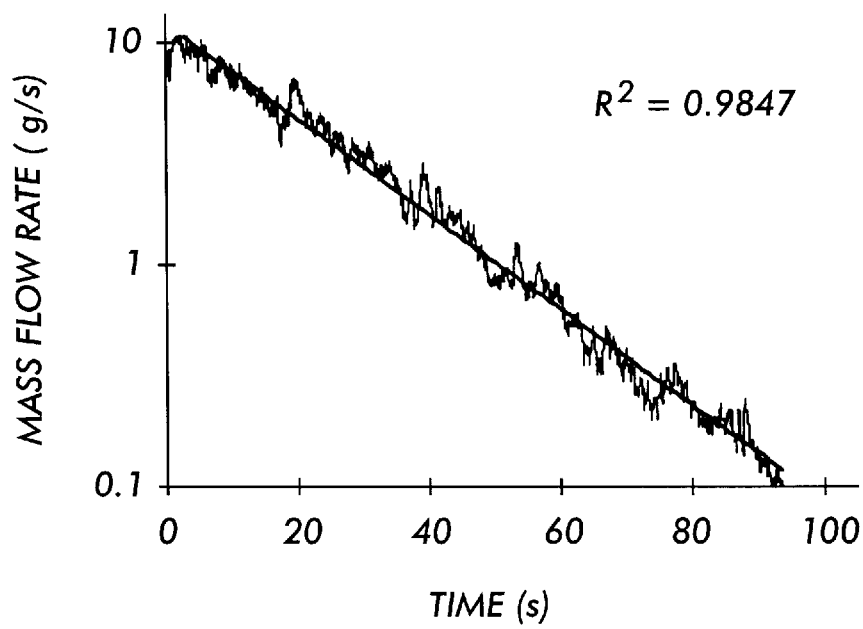
FIG. 14A depicts a mass flow rate vs. time where poor mixing has occurred.
Figure 14B:
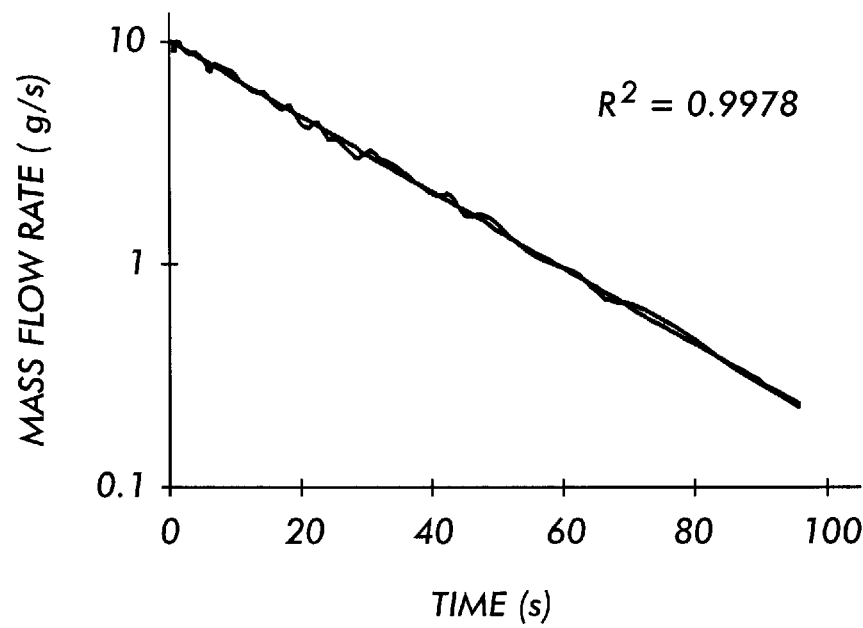
FIG. 14B depicts a mass flow rate vs. time where good mixing has occurred.

FIG. 14A shows mass flow rate with respect to time when there has been poor mixing of the mixture. As a result the mass flow rate shows up as large peak-to-peak swing of signal and the standard deviation from the reference line may not be tolerated for quality control. On the other hand, when there is a good mixing of the mixture, the standard deviation from the reference line is small and may be within the tolerance for quality control as shown in FIG. 14B. It should be understood that the mass flow rate shown in FIGS. 14A–14B correspond to the MDCV shown in FIGS. 9–10, where the mass of the riser R/capillary tube 24 is decreasing. However, it should be understood that any of the MDCVs disclosed in this application can be used for the homogeneity determination.

Figure 15A:
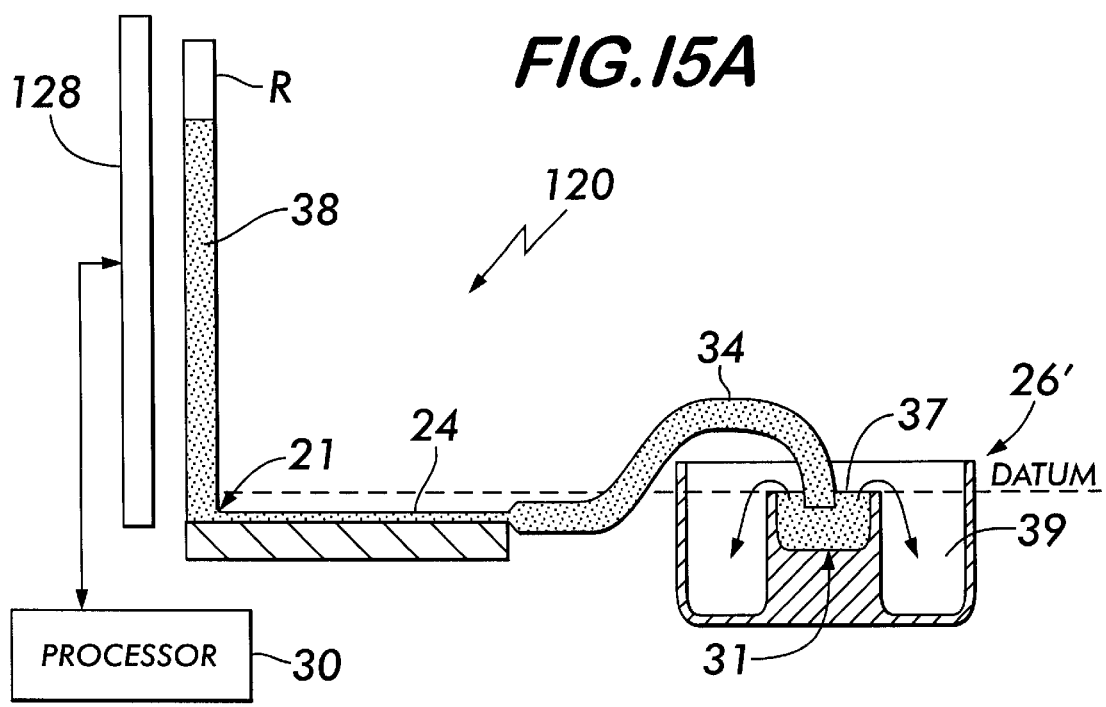
FIG. 15A depicts an SRSC viscometer using a column height detector known as a column height detection capillary (CHDC) viscometer.
Figure 15B:
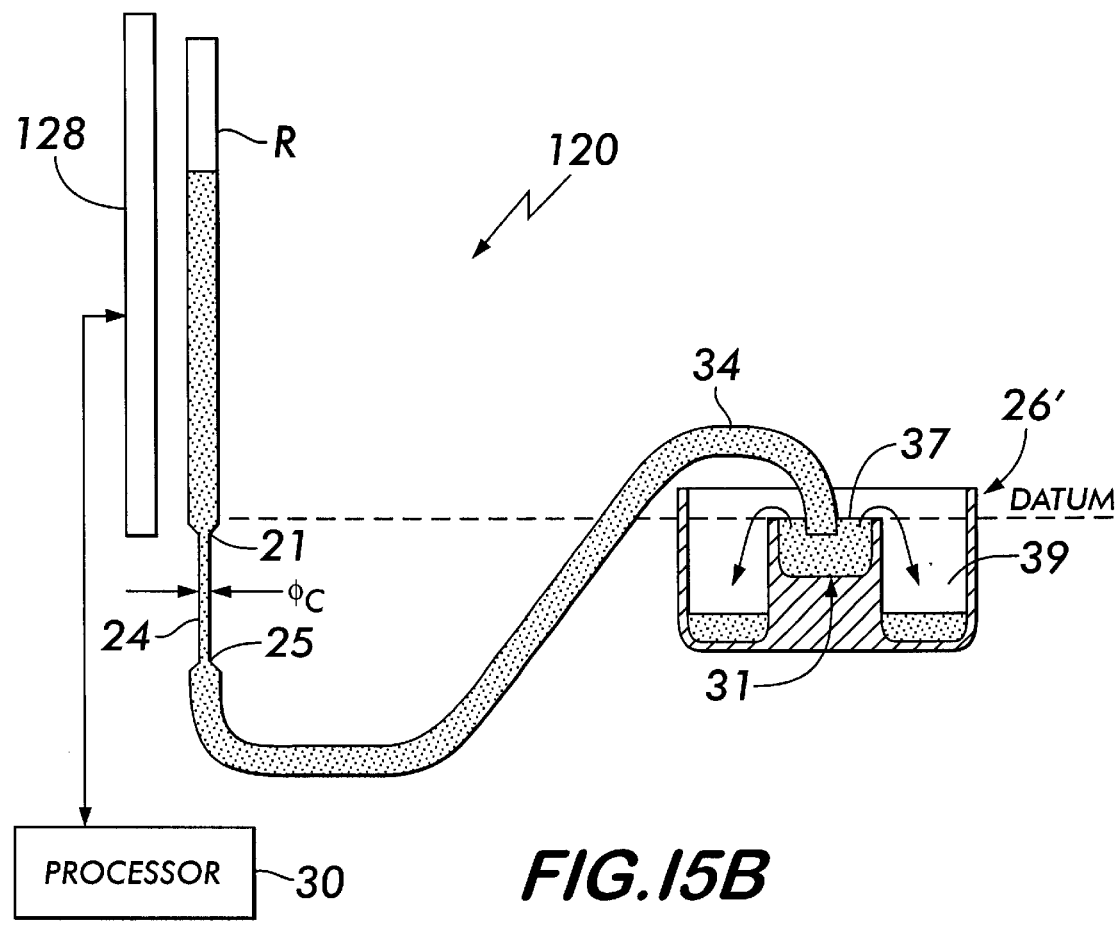
FIG. 15B depicts another embodiment of the CHDC viscometer.

FIGS. 15A–15B show two variations of the column height detection capillary (CHDC) viscometer 120. FIG. 15A depicts the CHDC viscometer 120 whereby the flow restrictor 24 is in a horizontal position and FIG. 15B depicts the CHDC viscometer 120 whereby the flow restrictor 24 is in a vertical position.

The CHDC viscometer 120 is similar to the MDCV 20 except that the mass detector 28 has been replaced by a column level detector 128. The column level detector 128 detects the changing height of the column 38 over time; in other words, the CHDC 120 is able to detect $\Delta h(t)$ directly (see Equation 4 above), instead of detecting that parameter indirectly by measuring the change of mass over time, m(t); see Equation 5 above. Thus, $h_i$ and $h_\infty$ can be obtained by the detector. As a result, the viscosity of both Newtonian fluids and non-Newtonian fluids can be determined using the CHDC viscometer 120. In particular, it can be shown that:

$$\mu = \frac{\rho g \phi_c^4}{32 \phi_R^2 L_c} \left( \frac{h_i - h_\infty - \Delta h(t)}{\frac{dh(t)}{dt}} \right), \quad (19)$$

for Newtonian fluids; and $$\eta = \frac{\rho g \phi_c^4}{8 L_c \phi_R^2} \left( \frac{h_i - h_\infty - \Delta h(t)}{\frac{dh(t)}{dt} \left( 3 + \frac{1}{n'} \right)} \right), \quad (20)$$

for non-Newtonian fluids.

In all other aspects, operation of the CHDC viscometer 120 is similar to that of the MDCV 20, including the sequence of running the viscosity test as set forth in FIGS. 11A–11D, and including the orientation of the riser tube R with respect to a horizontal reference position, etc.

It should be understood that the column level detector 128 may comprise the column level detectors disclosed in application Ser. No. 09/439,795 or application Ser. No. 09/573,267, both of whose entire disclosures are incorporated by reference herein. Furthermore, it should be understood that the use of the column level detector is by way of example only and that any method, known in the art, of detecting the movement of the column 38, e.g., using time of flight detection (e.g., an ultrasonic signal) against the trailing surface of the column 38, is within the broadest scope of this invention.

Without further elaboration, the foregoing will so fully illustrate our invention and others may, by applying current or future knowledge, readily adapt the same for use under various conditions of service.

We claim:

1. A method for determining the online viscosity of a fluid flowing through a process, said method comprising the steps of:

(a) providing a lumen having a first end and a second end, said first end being coupled to the process through a valve and wherein said lumen is positioned at an angle to a horizontal reference greater than zero degrees, said lumen having a first known dimension;

(b) coupling an inlet of a flow restrictor, having an outlet, to said second end of said lumen, said flow restrictor having some known dimensions;

(c) disposing a collector on a weight detector and positioning said outlet to deliver any fluid flowing through said outlet into said collector;

(d) opening said valve to allow a predetermined amount of fluid from the process to pass through said lumen and said flow restrictor and to collect in said collector to submerge said outlet and to form a continuous sample of fluid occupying said lumen and said flow restrictor, said opening of said valve establishing a pressure differential between said first end and said outlet;

(e) obtaining an initial weight of said collector by said weight detector;

(f) further controlling said valve to vent said first end to atmospheric pressure to cause said sample of fluid to move through said lumen and said flow restrictor at a first shear rate caused by said pressure differential, said movement of fluid causing said pressure differential to decrease from said first shear rate for generating said plural shear rates;

(g) detecting the changing weight of said collector over time as said sample of fluid passes through said outlet into said collector while maintaining said outlet being submerged in the fluid in said collector; and (h) calculating the online viscosity of the fluid based on the changing weight of said collector over time, said first known dimension and said some known dimensions.

2. The method of claim 1 wherein said flow restrictor is a capillary tube and wherein said step of calculating the viscosity comprises determining the pressure drop across said capillary tube, $\Delta P_c$, according to:

$$\Delta P_c = \frac{4g}{\pi \phi_R^2} [m_\infty - m_i - m(t)]$$

where, g is gravitational acceleration;

$\phi_R$ is the diameter of said lumen;

$m_\infty g$ is the final weight of said collector after a long period of time;

$m_{ig}$ is the initial weight of said collector before said sample of fluid starts moving; and $m(t)_g$ is the changing weight of the collector over time.

3. The method of claim 2 wherein the fluid is a Newtonian fluid and wherein said step of calculating the viscosity of the fluid comprises determining the viscosity of the Newtonian fluid, $\mu$, according to:

$$\mu = \frac{\rho g \phi_c^4}{32 \phi_R^2 L_c} \left( \frac{m_\infty - m_i - m(t)}{\frac{dm(t)}{dt}} \right)$$

where, $\rho$ is the density of the fluid;

$\phi_c$ is the diameter of said capillary tube; and $L_c$ is the length of said capillary tube.

4. The method of claim 2 wherein the fluid is a non-Newtonian fluid and said step of calculating the viscosity of the fluid comprises determining the viscosity, $\eta$, of the non-Newtonian fluid according to:

$$\eta = \frac{\rho g \phi_c^4}{8 L_c \phi_R^2} \frac{[m_\infty - m_i - m(t)]}{\left(\frac{dm}{dt}\right)\left(3 + \frac{1}{n'}\right)}$$

where, $\rho$ is the density of the fluid;

$\phi_c$ is the diameter of said capillary tube;

$L_c$ is the length of said capillary tube; and $$\frac{1}{n'} = \frac{d \ln Q}{d \ln \tau_w},$$

where

Q is the volumetric flow rate through said capillary tube; and $\tau_w$ is $\frac{\Delta P_c \phi_c}{4 L_c}$.

5. The method of claim 4 wherein the quantity $$\frac{1}{n'}$$

can be approximated by $$\frac{1}{n}$$

where n is the exponent of a power law constitutive equation.

6. The method of claim 1 wherein said step of disposing said collector on a weight detector comprises placing said collector on a precision balance or load cell.

7. The method of claim 6 wherein said valve and said precision balance or load cell are isolated from vibration caused by the process.

8. The method of claim 2 wherein said step of coupling an inlet of a flow restrictor, having an outlet, to said second end of said lumen comprises positioning said lumen and flow restrictor in a vertical position and wherein said inlet is located below a fluid level in said collector.

9. A method for determining the online viscosity of a fluid flowing through a process, said method comprising the steps of:
   (a) providing a lumen having a first end and a second end, said first end being coupled to the process through a valve and wherein said lumen is positioned at an angle to a horizontal reference greater than zero degrees, said lumen having a first known dimension;
   (b) coupling an inlet of a flow restrictor, having an outlet, to said second end of said lumen, said flow restrictor having some known dimensions;
   (c) providing a collector and positioning said outlet to deliver any fluid flowing through said outlet into said collector;
   (d) positioning said lumen on a weight detector;
   (e) opening said valve to allow a predetermined amount of fluid from the process to pass through said lumen and said flow restrictor and to collect in said collector to submerge said outlet and to form a continuous sample of fluid occupying said lumen and said flow restrictor, said opening of said valve establishing a pressure differential between said first end and said outlet;
   (f) obtaining an initial weight of said lumen by said weight detector;
   (g) further controlling said valve to vent said first end to atmospheric pressure to cause said sample of fluid to move through said lumen and said flow restrictor at a first shear rate caused by said pressure differential, said movement of fluid causing said pressure differential to decrease from said first shear rate for generating said plural shear rates;
   (h) detecting the changing weight of said lumen over time as said sample of fluid passes through said outlet into said collector while maintaining said outlet being submerged in the fluid in said collector; and
   (i) calculating the online viscosity of the fluid based on the changing weight of said lumen over time, said first known dimension and said some known dimensions.

10. The method of claim 9 wherein said flow restrictor is a capillary tube and wherein said step of calculating the viscosity comprises determining the pressure drop across said capillary tube, $\Delta P_c$, according to:

$$\Delta P_c = \frac{4g}{\pi \phi_R^2}[m_i - m_\infty - m(t)]$$

where, g is gravitational acceleration;

$\phi_R$ is the diameter of said lumen;

$m_\infty$ is the final weight of said lumen after a long period of time;

$m_i$ is the initial weight of said lumen before said sample of fluid starts moving; and m(t) is the changing weight of said lumen over time.

11. The method of claim 10 wherein the fluid is a Newtonian fluid and wherein said step of calculating the viscosity of the fluid comprises determining the viscosity of the Newtonian fluid, $\mu$, according to:

$$\mu = \frac{\rho g \phi_c^2}{32 L_c}\left(\frac{m_i - m_\infty - m(t)}{\frac{dm(t)}{dt}}\right)$$

where, $\rho$ is the density of the fluid;

$\phi_c$ is the diameter of said capillary tube; and $L_c$ is the length of said capillary tube.

12. The method of claim 10 wherein the fluid is a non-Newtonian fluid and said step of calculating the viscosity of the fluid comprises determining the viscosity, $\eta$, of the non-Newtonian fluid according to:

$$\eta = \frac{\rho g \phi_c^4}{8 L_c \phi_R^2} \frac{[m_i - m_\infty - m(t)]}{\left(\frac{dm}{dt}\right)\left(3 + \frac{1}{n'}\right)}$$

where, $\rho$ is the density of the fluid;

$\phi_c$ is the diameter of said capillary tube;

$L_c$ is the length of said capillary tube; and $$\frac{1}{n'} = \frac{d\ln Q}{d\ln \tau_w},$$

where

Q is the volumetric flow rate through said capillary tube; and $\tau_w$ is $$\frac{\Delta P_c \phi_c}{4 L_c}.$$

13. The method of claim 12 wherein the quantity $$\frac{1}{n'}$$

can be approximated by $$\frac{1}{n}$$

where n is the exponent of a power law constitutive equation.

14. The method of claim 9 wherein said step of disposing said lumen on a weight detector comprises placing said lumen on a precision balance or load cell.

15. The method of claim 14 wherein said valve and said precision balance or load cell are isolated from vibration caused by the process.

16. The method of claim 15 wherein said step of positioning said lumen on a precision balance or load cell comprises:
    flush-mounting an open end of said lumen on said precision balance or load cell to form an interface between said open end and said precision balance or load cell; and
    sealing said interface.

17. The method of claim 15 wherein said step of positioning said lumen on a precision balance or load cell comprises closing off an open end of said lumen with a pliable membrane and positioning said lumen on said precision balance or load cell.

* * * * *